(12) United States Patent
Iwama et al.

(10) Patent No.: US 9,561,255 B2
(45) Date of Patent: *Feb. 7, 2017

(54) COSMETIC, EXTERNAL SKIN PREPARATION, AND MEDICAL INSTRUMENT

(71) Applicants: NISSAN CHEMICAL INDUSTRIES, LTD., Tokyo (JP); KYUSHU UNIVERSITY, NATIONAL UNIVERSITY CORPORATION, Fukuoka-shi, Fukuoka (JP)

(72) Inventors: Takehisa Iwama, Funabashi (JP); Keigo Matsumoto, Funabashi (JP); Takayuki Imoto, Funabashi (JP); Nobuhide Miyachi, Tokyo (JP); Masahiro Goto, Fukuoka (JP)

(73) Assignees: NISSAN CHEMICAL INDUSTRIES, LTD., Tokyo (JP); KYUSHU UNIVERSITY, NATIONAL UNIVERSITY CORPORATION, Fukuoka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,202

(22) Filed: Nov. 26, 2012

(65) Prior Publication Data
US 2013/0084305 A1 Apr. 4, 2013

Related U.S. Application Data

(62) Division of application No. 13/504,026, filed as application No. PCT/JP2010/069012 on Oct. 26, 2010, now Pat. No. 8,999,300.

(30) Foreign Application Priority Data
Oct. 26, 2009 (JP) ................. 2009-245380

(51) Int. Cl.
| | |
|---|---|
| A61K 38/05 | (2006.01) |
| A61K 38/39 | (2006.01) |
| A61K 31/734 | (2006.01) |
| A61K 31/715 | (2006.01) |
| A61K 8/64 | (2006.01) |
| A61K 9/00 | (2006.01) |
| A61K 9/06 | (2006.01) |
| A61K 47/10 | (2006.01) |
| A61K 47/42 | (2006.01) |
| A61L 15/28 | (2006.01) |
| A61L 26/00 | (2006.01) |
| A61Q 19/00 | (2006.01) |
| A61K 9/12 | (2006.01) |
| A61K 47/36 | (2006.01) |

(Continued)

(52) U.S. Cl.
CPC ............ *A61K 38/05* (2013.01); *A61K 8/64* (2013.01); *A61K 9/0014* (2013.01); *A61K 9/06* (2013.01); *A61K 31/715* (2013.01); *A61K 31/734* (2013.01); *A61K 38/39* (2013.01); *A61K 47/10* (2013.01); *A61K 47/42* (2013.01); *A61L 15/28* (2013.01); *A61L 26/0023* (2013.01); *A61Q 19/00* (2013.01); *A61K 47/36* (2013.01); *A61K 47/48038* (2013.01); *A61K 2800/48* (2013.01); *A61L 2400/04* (2013.01); *A61Q 19/02* (2013.01); *A61Q 19/08* (2013.01); *C07K 5/06026* (2013.01)

(58) Field of Classification Search
None
See application file for complete search history.

(56) References Cited

U.S. PATENT DOCUMENTS 4,920,158 A  4/1990 Murray et al.
5,254,338 A  10/1993 Sakai et al.
(Continued)

FOREIGN PATENT DOCUMENTS

CN  1458848 A  11/2003
EP  2 246 073 A1  11/2010
(Continued)

OTHER PUBLICATIONS

Shinji Matsumoto and Itaru Hamachi, The Supramolecular Hydrogel toward "The Smart Biomaterials", *Dojin News* No. 118, 1-16, (2006).
Lara A. Estroff and Andrew D. Hamilton, Water Gelation by Small Organic Molecules, *Chemical Reviews*, (2004), vol. 104, No. 3, pp. 1201-1217.
Masahiro Suzuki, et al., Supramolecular Hydrogels Formed by L-Lysine Derivatives, *Chemistry Letters*, (2004), vol. 33, No. 11, pp. 1496-1497.
Jong Hwa Jung, et al., Self-Assembly of a Sugar-Based Gelator in Water: Its Remarkable Diversity in Gelation Ability and Aggregate Structure, *Langmuir*, (2001), vol. 17, pp. 7229-7232.
Itaru Hamachi, et al., Solid-phase lipid synthesis (SPLS)-2: incidental discovery of organogelators based on artificial glycolipids, *Tetrahedron Letters*, (2001), vol. 42, pp. 6141-6145.
Itaru Hamachi, et al., Solid phase lipid synthesis (SPLS) for construction of an artificial glycolipid library, *Chem. Commun.* (2000), p. 1281-1282.
(Continued)

*Primary Examiner* — Mina Haghighatian
*Assistant Examiner* — Luke Karpinski
(74) *Attorney, Agent, or Firm* — Oliff PLC

(57) ABSTRACT

It is an object of the present invention to provide a cosmetic or external skin preparation that has an improved feel in use, e.g., excellent stretching on the skin surface, excellent permeation into the skin, and no stickiness, or crinkles. A cosmetic or an external skin preparation, and a medical instrument, comprising at least one lipid peptide-based gelator that contains a low-molecular lipid peptide of Formula (1):

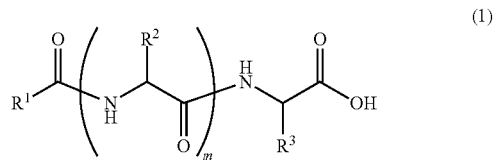

(where $R^1$ to $R^3$ are independently an organic group) or a pharmaceutically usable salt thereof.

1 Claim, 3 Drawing Sheets

(51) Int. Cl.
*A61Q 19/02* (2006.01)
*A61Q 19/08* (2006.01)
*A61K 47/48* (2006.01)
*C07K 5/062* (2006.01)

(56) References Cited

U.S. PATENT DOCUMENTS

| | | | |
|---|---|---|---|
| 5,693,624 A | 12/1997 | Hardy et al. | |
| 6,706,279 B1* | 3/2004 | Hazzi | 424/443 |
| 8,058,499 B2* | 11/2011 | Silcock et al. | 602/48 |
| 2003/0165560 A1* | 9/2003 | Otsuka et al. | 424/445 |
| 2005/0129633 A1 | 6/2005 | Lin | |
| 2007/0048245 A1 | 3/2007 | Belfer | |
| 2007/0099842 A1 | 5/2007 | Ziegler et al. | |
| 2010/0279955 A1* | 11/2010 | Miyachi et al. | 514/21.9 |
| 2010/0291210 A1* | 11/2010 | Miyachi et al. | 424/484 |
| 2011/0183913 A1* | 7/2011 | Miyamoto et al. | 514/18.8 |

FOREIGN PATENT DOCUMENTS

| | | |
|---|---|---|
| JP | A-8-187280 | 7/1996 |
| JP | A-9-255524 | 9/1997 |
| JP | A-11-292750 | 10/1999 |
| JP | A-2000-226311 | 8/2000 |
| JP | A-2004-203825 | 7/2004 |
| JP | A-2005-35947 | 2/2005 |
| JP | A-2007-269746 | 10/2007 |
| JP | A-2007-269747 | 10/2007 |
| JP | A-2008-143878 | 6/2008 |
| JP | A-2009-40716 | 2/2009 |
| JP | A-2009-120510 | 6/2009 |
| WO | WO 02/22182 A1 | 3/2002 |
| WO | WO 2009/005151 A1 | 1/2009 |
| WO | WO 2009/005152 A1 | 1/2009 |
| WO | WO 2009/107189 A1 | 9/2009 |
| WO | WO 2010/013555 A1 | 2/2010 |
| WO | WO 2010/147158 A1 | 12/2010 |

OTHER PUBLICATIONS

Masahiro Suzuki, et al., Supramolecular hydrogel formed by glucoheptonamide of L-lysine: simple preparation and excellent hydrogelation ability, *Tetrahedron*, (2007), vol. 63, pp. 7302-7308.
Yoko Matsuzawa, et al., Assembly and Photoinduced Organization of Mono- and Oligopeptide Molecules Containing an Azobenzene Moiety, *Advanced Functional Materials*, (2007), vol. 17, pp. 1507-1514.
Feb. 22, 2013 Office Action issued in U.S. Appl. No. 13/504,026.
Feb. 16, 2013 First Office Action issued in Chinese Application No. 201080048460.1 with English-language translation.
Nov. 5, 2013 Office Action issued in U.S. Appl. No. 13/504,026.
Hartgerink et al., "Self-Assembly and Mineralization of Peptide-Amphiphile Nanofibers," Science, vol. 294, No. 5547, pp. 1684-1688, Nov. 23, 2001.
Feb. 7, 2014 Supplementary European Search Report issued in European Application No. 10826745.1.
Nov. 18, 2013 Office Action issued in Chinese Application No. 201210301128.2 (with English translation).
Oct. 9, 2014 Office Action issued in European Application No. 12 182 362.9.

* cited by examiner

EVALUATION RESULTS OF BLOOD COAGULATION (HEMOSTATIC EFFECT)

| BLOOD COAGULATING SUBSTANCE (1%) | | 1%Pal-GH | | 10%CMC |
|---|---|---|---|---|
| NONE | REFERENCE EXAMPLE 1 | | REFERENCE EXAMPLE 2 | |
| GELATIN | EXAMPLE 26 | | COMPARATIVE EXAMPLE 6 | |
| SODIUM ALGINATE | EXAMPLE 27 | | COMPARATIVE EXAMPLE 7 | |
| PROPYLENE GLYCOL ALGINATE | EXAMPLE 28 | | COMPARATIVE EXAMPLE 8 | |
| GUM ARABIC | EXAMPLE 29 | | COMPARATIVE EXAMPLE 9 | |

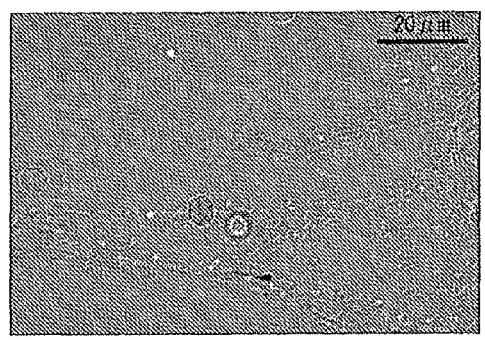

Pal-GH
REFERENCE EXAMPLE 1

4(b)

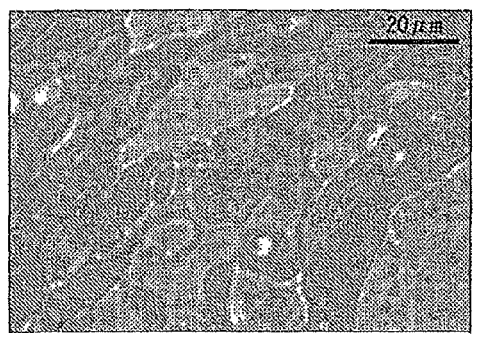

CMC
REFERENCE EXAMPLE 2

FIG. 5
5(a)
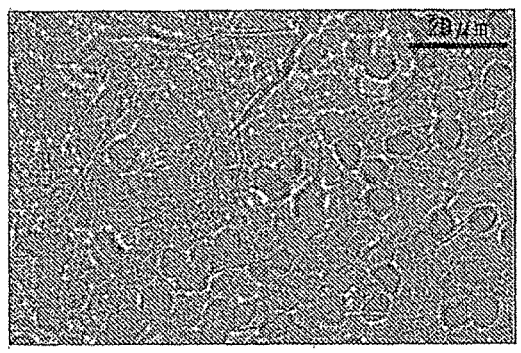
Pal-GH + SODIUM ALGINATE
EXAMPLE 27
5(b)
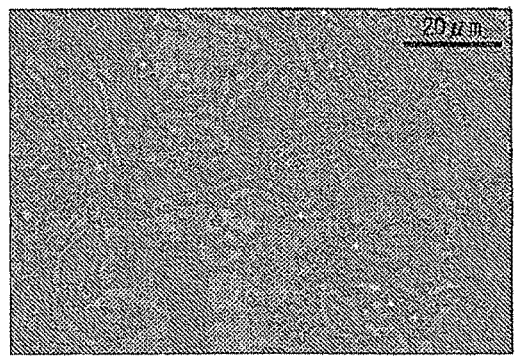
CMC + SODIUM ALGINATE
COMPARATIVE EXAMPLE 7
FIG. 6
6(a)
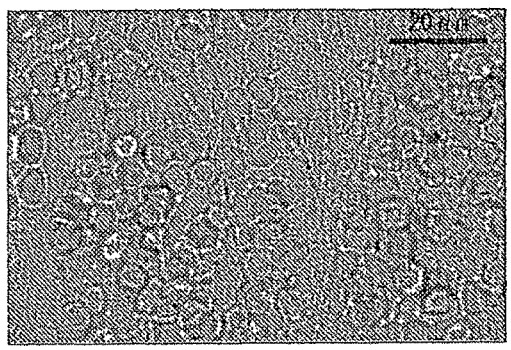
Pal-GH + GUM ARABIC
EXAMPLE 29
6(b)
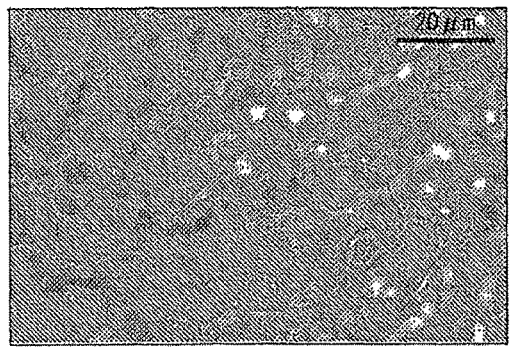
CMC + GUM ARABIC
COMPARATIVE EXAMPLE 9

COSMETIC, EXTERNAL SKIN PREPARATION, AND MEDICAL INSTRUMENT

PARTIES TO A JOINT RESEARCH AGREEMENT

This application is a result of activities undertaken within the scope of a joint research agreement between Nissan Chemical Industries, Ltd. and Kyushu University, National University Corporation that was in effect on or before the date the research leading to this application was made.

TECHNICAL FIELD

The present invention relates to a cosmetic, an external skin preparation, and a medical instrument that include at least one lipid peptide-based gelator. More specifically, the present invention relates to a cosmetic, an external skin preparation, and a medical instrument that include a lipid peptide-based gelator, the lipid peptide-based gelator containing a lipid peptide with a molecular weight of 1,000 or less or a pharmaceutically usable salt thereof.

BACKGROUND ART

Conventionally, research has been conducted on cosmetics that make the skin firm and elastic. As the cosmetics that make the skin firm and elastic, cosmetics that are formulated with a moisturizing component having excellent water retention and excellent water absorbency, such as various water-soluble polyhydric alcohols, mucopolysaccharides, and polymers, and cosmetics that are formulated with an active ingredient for making the skin firm and elastic such as plant extracts are commercially available. Cosmetics that are formulated with these components are improved in the effect of making the skin firm and elastic; however, such cosmetics have problems of having less preferable feel in use, e.g., poor permeation into the skin or lingering stickiness. A cosmetic that is formulated with glycerin or other polyhydric alcohols is known to have a problem of causing stickiness that is likely to linger on the skin (Patent Document 1).

In order to solve these conventional problems, various cosmetics have been developed by considering the types and the formulation amounts of moisturizing components to be formulated. For example, a method for formulating a polymer having a basic amino acid residue in the structure and a macromolecule (xanthan gum) in combination (Patent Document 2), a method for formulating raffinose and agar-agar in combination (Patent Document 3), a method for formulating glycol and an adduct of diglycerin with propylene oxide in combination (Patent Document 4), and the like have been developed. Besides, a method for formulating a component that has an effect of inhibiting a collagenase, which is one of the causes of making the skin less firm and less elastic (Patent Document 5) and a method for formulating dimer linoleyl bis(phytosteryl/behenyl/isostearyl) dimer dilinoleate and gellan gum in combination at a certain amount (Patent Document 6) have also been developed. However, these methods cannot yet produce a cosmetic or an external skin preparation that has excellent texture in use, e.g., no crinkles of a cosmetic or smooth application.

A skin cosmetic (eye cream) that is prepared using a water dispersion of urethane resin that is synthesized by a reaction of a polyol compound and an isocyanate compound is recently reported. The use of the skin cosmetic is reported to give a feeling of improved wrinkles on the skin and a feeling of improved sagging (a feeling of firmer skin), and to have an improved feel in use, e.g., less stickiness, less crinkles of a cosmetic on the skin, and less unsmooth application (Patent Document 7). However, little studies have been conducted on this type of cosmetics other than eye creams regarding the feel in use, e.g., crinkles or unsmooth application. Currently, development of a cosmetic and an external skin preparation is longed for that is excellent in permeation into the skin, is excellent in stretching on the skin, and has no unpleasant feel in use, e.g., stickiness, crinkles on the skin, or unsmooth application.

Polymer gel (chemical gel and physical gel) that is obtained by crosslinking of macromolecular compounds via a covalent bond, an ionic bond, a hydrogen bond, or the like is known. It is known that the more polymer gel a product contains, the more viscous the product is, and as a result, dripping is less likely to occur, rubbing the product into fingers is easier, and the scattering of the product when rubbed is prevented. However, it has been pointed out that high polymer gel content causes stickiness (Patent Documents 8 and 9) and causes crinkles when drying (Patent Document 10). Conversely, a cosmetic that contains less polymer gel is less likely to cause stickiness and crinkles, but it is more prone to drip and is less easily rubbed into fingers. Enough studies have not yet been conducted on the feel in use, e.g., stickiness and crinkles on the skin, and therefore a method that can collectively solve dripping, stickiness, and crinkles is desired.

Meanwhile, interest in anti-aging technologies and tissue engineering has grown rapidly, and development of a cosmetic that is highly biocompatible and highly safe has been desired. In recent years, hydrogels are used in various fields as a highly biocompatible material having water as a medium, and most of the hydrogels are a hydrogel that includes a macromolecular compound or a hydrogel that is formulated with an inorganic material, namely a hydrophobized powder. When these hydrogels are used in a cosmetic or an external skin preparation, however, these hydrogels have problems of an unreacted substance resulting from the synthesis of the macromolecular compound and of the safety of the inorganic material itself.

In recent years, active research on a low-molecular hydrogelator containing a low-molecular compound has been conducted, because the functions of the low-molecular hydrogelator have attracted a lot of interest despite the fact that determination of a mechanism of self-organization among low-molecular compounds in water and molecular design are difficult. As a result, some low-molecular hydrogelators have been discovered (Non-patent Documents 1 and 2). Most of them are amphiphilic compounds that have both a long-chain alkyl group as a hydrophobic moiety and a hydrophilic moiety, and examples of these include ones having an amino acid (Non-patent Document 3), ones having a peptide (Patent Documents 11 and 12), ones having a mono- or polysaccharide (Non-patent Documents 4, 5, and 6), and ones having a polyol (Non-patent Document 7), as the hydrophilic moiety. A low-molecular gelator has been developed utilizing the fact that a peptide including valine easily assumes a β-sheet structure (Non-patent Document 8).

Low-molecular hydrogelators that cannot gel water alone nor organic solvent alone but gel aqueous alcohol solutions and/or organic solvent aqueous solutions have been reported. A well-known common characteristic of low-molecular gel is to quickly react to external stress to convert from gel to sol.

RELATED ART DOCUMENTS

Patent Documents

Patent Document 1: Japanese Patent Application Publication No. JP-A-11-292750
Patent Document 2: Japanese Patent Application Publication No. JP-A-2005-35947
Patent Document 3: Japanese Patent Application Publication No. JP-A-2007-269747
Patent Document 4: Japanese Patent Application Publication No. JP-A-9-255524
Patent Document 5: Japanese Patent Application Publication No. JP-A-2000-226311
Patent Document 6: Japanese Patent Application Publication No. JP-A-2007-269746
Patent Document 7: Japanese Patent Application Publication No. JP-A-2009-120510
Patent Document 8: Japanese Patent Application Publication No. JP-A-2008-143878
Patent Document 9: Japanese Patent Application Publication No. JP-A-2009-40716
Patent Document 10: Japanese Patent Application Publication No. JP-A-2004-203825
Patent Document 11: International Publication No. WO 2009/005151 pamphlet
Patent Document 12: International Publication No. WO 2009/005152 pamphlet Non-Patent Documents Non-patent Document 1: Shinji Matsumoto, Itaru Hamachi, DOJIN NEWS No. 118, 1-16 (2006)
Non-patent Document 2: Lara A. Estroff and Andrew D. Hamilton, Chemical Review. 2004, 104, 1201-1217
Non-patent Document 3: Suzuki, Masahiro. Yumoto, Mariko. Kimura, Mutsumi. Shirai, Hirofusa. Hanabusa, Kenji. Chemistry Letters, 2004, 33(11), 1496-1497
Non-patent Document 4: Jong Hwa Jung, Geoerg John, Mitsutoshi Masuda, Kaname Yoshida, Seiji Shinkai, and Toshimi Shimizu Langmuir, 2001, 17, 7229-7232
Non-patent Document 5: I. Hamachi, S. Kiyonaka, S. Shinkai, Tetrahedron Lett., 2001, 42, 6141
Non-patent Document 6: I. Hamachi, S. Kiyonaka, S. Shinaki, Chem. Commun., 2000, 1281
Non-patent Document 7: Masahiro Suzuki, Sanae Owa, Hirofusa Shirai and Kenji Hanabusa, Tetrahedron 2007 63 7302-7308
Non-patent Document 8: Yoko Matsuzawa, Katsuyuki Ueki, Masaru Yoshida, Nobuyuki Tamaoki, Tohru Nakamura, Hideki Sakai, and Masahiko Abe, Adv. Funct. Mater. 2007, 17, 1507-1514

SUMMARY OF THE INVENTION

Problem to be Solved by the Invention

As described above, a cosmetic or an external skin preparation is required to include a highly biocompatible, highly safe material. In addition, a cosmetic or an external skin preparation in a cream form, a gel form, or other dosage form is required to have an excellent characteristic (namely, excellent stretching on the skin surface and the hair surface) that the cosmetic (or the external skin preparation) stretches smoothly on the skin surface and the hair surface without roughness when applied on the skin and the hair, and to have an excellent characteristic (namely, excellent permeation into the skin and the hair) that the cosmetic (or the external skin preparation) rapidly permeates the skin and the hair and is absorbed into the skin and the hair to moisturize them. A cosmetic or an external skin preparation is further required to have an excellent feel in use, e.g., after applied, no stickiness lingering on the skin surface and the hair surface and, particularly at active parts, such as joints, that are subject to frequent and intense motion, or no streaks (namely, crinkles) formed by crinkled cosmetic or external skin preparation. A cosmetic or an external skin preparation in a liquid form, a sol form, or other dosage form is also required, in addition to excellent stretching on the skin surface and the hair surface, excellent premeation into the skin and the hair, and no stickiness or crinkles, to cause no dribbling of the cosmetic or the external skin preparation from the skin, namely, to cause no dripping, when poured onto the hand or sprayed. No conventional cosmetic or conventional external skin preparation collectively fulfills these requirements.

In recent years, a hydrogel that is formulated with a gelator containing a low-molecular compound has been developed as the highly biocompatible, highly safe material, but no cosmetic, external skin preparation, or medical instrument that is formulated with the gelator has been developed.

The present invention is devised based on the above circumstances, and an object of the present invention is to provide a cosmetic or an external skin preparation that is highly biocompatible and highly safe, has an improved feel in use, e.g., improved stretching on the skin surface and the hair surface and improved permeation into the skin and the hair when applied, or no stickiness or crinkles caused after applied, and when the cosmetic or the external skin preparation is in a liquid form, a sol form, or other dosage form, causes no dripping when applied. Another object of the present invention is to provide a medical instrument such as wound dressing base materials and hemostatic agent base materials that is highly biocompatible and highly safe.

Means for Solving the Problem

The inventors of the present invention have made intensive research to solve these problems, and as a result, have now found the present invention.

Namely, as a first aspect, a cosmetic or an external skin preparation is characterized by including at least one lipid peptide-based gelator that contains a low-molecular lipid peptide or a pharmaceutically usable salt thereof.

As a second aspect, in the cosmetic or the external skin preparation according to the first aspect, a molecular weight of the low-molecular lipid peptide is 1,000 or less.

As a third aspect, in the cosmetic or the external skin preparation according to the first or the second aspect, the low-molecular lipid peptide is represented by Formula (1):

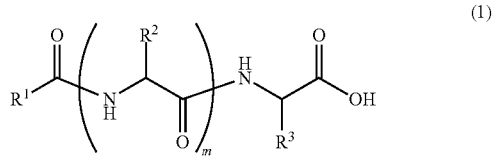

(where $R^1$ is a $C_{9-23}$ aliphatic group, $R^2$ and $R^3$ are independently a hydrogen atom, a methyl group, an ethyl group, a $C_{3-7}$ alkyl group that optionally contains a $C_{1-3}$ branched chain, a phenylmethyl group, a phenylethyl group, or a —(CH$_2$)n-X group, at least one of R$^2$ and R$^3$ is a —(CH$_2$)n-X group, n is a number of 1 to 4, X is an amino group, a guanidino group, a carbamoyl group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms, and m is 1 to 3).

As a fourth aspect, in the cosmetic or the external skin preparation according to the third aspect, in Formula (1), R$^2$ is a hydrogen atom, a methyl group, an isopropyl group, an isobutyl group, or a sec-butyl group.

As a fifth aspect, in the cosmetic or the external skin preparation according to the third aspect, in Formula (1), R$^3$ is a 1-aminobutyl group, a 4-imidazole methyl group, a carbamoylmethyl group, a carbamoylethyl group, or a 3-methylindole group.

As a sixth aspect, in the cosmetic or the external skin preparation according to the third aspect, in Formula (1), R$^1$ is a C$_{13-17}$ aliphatic group, R$^2$ is a hydrogen atom, a methyl group, or an isopropyl group, and R$^3$ is a 4-aminobutyl group, a 4-imidazole methyl group, or a 3-methylindole group.

As a seventh aspect, in the cosmetic or the external skin preparation according to the sixth aspect, in Formula (1), R$^2$ is a hydrogen atom and R$^3$ is a 4-imidazole methyl group.

As an eighth aspect, in the cosmetic or the external skin preparation according to any one of the first to the seventh aspects, a concentration of the lipid peptide-based gelator is 0.00001% (w/v) to 50% (w/v) relative to a total volume of the cosmetic or the external skin preparation.

As a ninth aspect, the cosmetic or the external skin preparation according to any one of the first to the eighth aspects includes water, an alcohol, a polyhydric alcohol, a hydrophilic organic solvent, a hydrophobic organic solvent, or a miscible, mixed solution thereof.

As a tenth aspect, the cosmetic or the external skin preparation according to the ninth aspect includes water, or a miscible, mixed solution of water and one or more selected from the group consisting of alcohols, polyhydric alcohols, oils/fats, silicone oils, and ester solvents.

As an eleventh aspect, the cosmetic or the external skin preparation according to the tenth aspect includes water, or a miscible, mixed solution of water and one or more selected from the group consisting of ethanol, 2-propanol, oleoyl alcohol, phenoxy alcohol, glycerin, propylene glycol, polyethylene glycol, 1,3-butanediol, aqua jojoba oil, castor oil, olive oil, silicone oils, and propylene glycol alginic acid ester.

As a twelfth aspect, the cosmetic or the external skin preparation according to the ninth aspect includes a polyhydric alcohol, or a miscible, mixed solution of a polyhydric alcohol and one or more selected from the group consisting of alcohols, oils/fats, silicone oils, and ester solvents.

As a thirteenth aspect, the cosmetic or the external skin preparation according to the twelfth aspect includes one or more polyhydric alcohols selected from the group consisting of glycerin, propylene glycol, polyethylene glycol, and 1,3-butanediol, or a miscible, mixed solution of the polyhydric alcohol and one or more selected from the group consisting of ethanol, 2-propanol, oleoyl alcohol, phenoxy alcohol, aqua jojoba oil, castor oil, olive oil, silicone oils, and propylene glycol alginic acid ester.

As a fourteenth aspect, the cosmetic or the external skin preparation according to any one of the ninth to the thirteenth aspects further includes a surfactant, a disinfectant, a preservative, or a stabilizer.

As a fifteenth aspect, in the cosmetic or the external skin preparation according to the fourteenth aspect, the surfactant is benzalkonium.

As a sixteenth aspect, the cosmetic or the external skin preparation according to any one of the ninth to the fifteenth aspects further includes a hydrocarbon, a wax, a powder, a coloring material, or an anti-UV agent.

As a seventeenth aspect, the cosmetic or the external skin preparation according to any one of the ninth to the sixteenth aspects further includes a vitamin, a skin-brightening agent, an antioxidant, a physiologically active substance, or a functional substance.

As an eighteenth aspect, in the cosmetic or the external skin preparation according to the seventeenth aspect, the vitamin is vitamin C.

As a nineteenth aspect, in the cosmetic or the external skin preparation according to the seventeenth or the eighteenth aspect, the physiologically active substance is indomethacin or camphor.

As a twentieth aspect, the cosmetic or an external skin preparation according to any one of the first to the nineteenth aspects is characterized by being in the form of gel, cream, or sol (water dispersion), and being capable of achieving an excellent feel in use that includes excellent permeation into the skin and the hair, excellent stretching on the skin and the hair, and less stickiness and crinkles.

As a twenty-first aspect, the cosmetic or the external skin preparation according to the first aspect further includes at least one macromolecular compound.

As a twenty-second aspect, in the cosmetic or the external skin preparation according to the twenty-first aspect, the macromolecular compound is cellulose or a derivative thereof, alginic acid or a salt thereof, polyvinyl alcohol, hyaluronic acid or a salt thereof, or collagen.

As a twenty-third aspect, a medical instrument is characterized by including at least one lipid peptide-based gelator that contains a low-molecular lipid peptide or a pharmaceutically usable salt thereof, and at least one macromolecular compound.

As a twenty-fourth aspect, in the medical instrument according to the twenty-third aspect, the medical instrument is a wound dressing base material or a hemostatic agent base material.

As a twenty-fifth aspect, in the medical instrument according to the twenty-third aspect, the low-molecular lipid peptide is represented by Formula (1).

As a twenty-sixth aspect, in the medical instrument according to the twenty-third aspect, the macromolecular compound is a macromolecular compound having blood coagulating activity.

As a twenty-seventh aspect, in the medical instrument according to the twenty-third aspect, the macromolecular compound having blood coagulating activity is cellulose or a derivative thereof, alginic acid or a salt thereof, or gum arabic.

As a twenty-eighth aspect, in the medical instrument according to the twenty-seventh aspect, the macromolecular compound having blood coagulating activity is sodium alginate or gum arabic.

Effects of the Invention

The cosmetic or the external skin preparation of the present invention that includes a lipid peptide-based gelator, in which the lipid peptide has a low molecular weight, is highly biocompatible and highly safe, and has an improved feel in use, e.g., excellent stretching on the skin surface and the hair surface, excellent permeation into the skin and the hair, and no stickiness, crinkles, or dripping.

The cosmetic or the external skin preparation of the present invention that includes a lipid peptide-based gelator, in which the lipid peptide has a low molecular weight, and a macromolecular compound is highly biocompatible and highly safe, and has an improved feel in use, e.g., excellent stretching on the skin surface and the hair surface and excellent permeation into the skin and the hair.

The cosmetic, the external skin preparation, and the medical instrument of the present invention that include a lipid peptide-based gelator, in which the lipid peptide has a low molecular weight, and a macromolecular compound achieve a synergistic effect of the lipid peptide-based gelator, in which the lipid peptide has a low molecular weight, and the macromolecular compound.

BRIEF DESCRIPTION OF THE DRAWINGS

FIG. 3 is a table listing blood coagulation in Reference Examples 1 and 2, Examples 26 to 29, and Comparative Examples 6 to 9.

FIG. 4(a) and FIG. 4(b) are views of a microscope image (×1000) of blood coagulation in Reference Examples 1 and 2.

FIG. 5(a) and FIG. 5(b) are views of a microscope image (×1000) of blood coagulation in Example 27 and Comparative Example 7.

FIG. 6(a) and FIG. 6(b) are views of a microscope image (×1000) of blood coagulation in Example 29 and Comparative Example 9.

MODES FOR CARRYING OUT THE INVENTION

Lipid Peptide-Based Gelator

Figure 1:
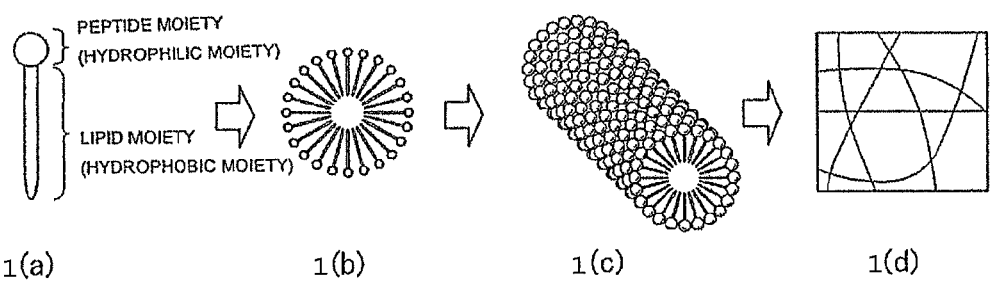
FIGS. 1(a)-1(d) are conceptual views of self-assembly and gelation of a lipid peptide-based gelator in a hydrophilic solution.

The cosmetic or the external skin preparation of the present invention is characterized by including at least one lipid peptide-based gelator that contains a lipid peptide or a pharmaceutically usable salt thereof.

The lipid peptide preferably has a molecular weight of 1,000 or less.

Examples of the low-molecular lipid peptide may include a lipid peptide that contains a lipid moiety and a peptide moiety of, for example, Formula (1).

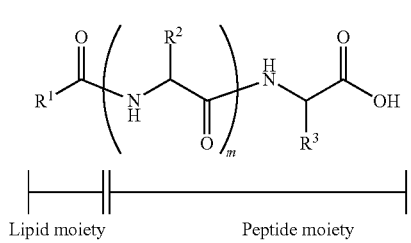

In Formula (1), $R^1$ is a $C_{9-23}$ aliphatic group and is preferably a $C_{13-17}$ aliphatic group.

Examples of the lipid moiety including $R^1$ and an adjacent carbonyl group may include a decoyl group, a dodecoyl group, an undecoyl group, a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, a vaccenoyl group, an octadecylcarbonyl group, an arachidonoyl group, an icosanoyl group, a behenoyl group, an erucoyl group, a docosylcarbonyl group, a lignoceroyl group, a nervonoyl group, and the like, and preferably include a myristoyl group, a tetradecylcarbonyl group, a palmitoyl group, a margaroyl group, an oleoyl group, an elaidoyl group, a linoleoyl group, a stearoyl group, a vaccenoyl group, and the like.

In Formula (1), $R^2$ and $R^3$ are independently a hydrogen atom, a methyl group, an ethyl group, a $C_{3-7}$ alkyl group that optionally contains a $C_{1-3}$ branched chain, a phenylmethyl group, a phenylethyl group, or a $—(CH_2)n-X$ group, at least one of $R^2$ and $R^3$ is a $—(CH_2)n-X$ group, n is a number of 1 to 4, and X is an amino group, a guanidino group, a carbamoyl group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms.

$R^2$ is preferably a hydrogen atom, a methyl group, an ethyl group, or a $C_{3-7}$ alkyl group that optionally contains a $C_{1-3}$ branched chain. Therefore, $R^2$ is preferably a hydrogen atom, a methyl group, an ethyl group, an n-propyl group, an isopropyl group, an n-butyl group, an isobutyl group, a sec-butyl group, a tert-butyl group, or the like, is further preferably a hydrogen atom, a methyl group, an isopropyl group, an isobutyl group, or a sec-butyl group, and is further more preferably a hydrogen atom.

$R^3$ is preferably a hydrogen atom, a methyl group, or a $—(CH_2)n-X$ group, n is a number of 1 to 4, and X is an amino group, a guanidino group, a $—CONH_2$ group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms.

In the $—(CH_2)n-X$ group as $R^3$, X is preferably an amino group, a guanidino group, a carbamoyl group, an imidazole group, a pyrazole group, or an indole group.

Therefore, the $—(CH_2)n-X$ group as $R^3$ is preferably an aminomethyl group, a 2-aminoethyl group, a 3-aminopropyl group, a 4-aminobutyl group, a carbamoylmethyl group, a 2-carbamoylethyl group, a 3-carbamoylpropyl group, a 2-guanidinoethyl group, a 3-guanidinopropyl group, a pyrrole methyl group, a 4-imidazole methyl group, a pyrazole methyl group, or a 3-indole methyl group, is more preferably a 4-aminobutyl group, a carbamoylmethyl group, a carbamoylethyl group, a 3-carbamoylpropyl group, a 4-imidazole methyl group, or a 3-indole methyl group, and is further more preferably a 4-imidazole methyl group.

In Formula (1), m that is the number of the repeating peptide structures is 1 to 3.

As for the compound of Formula (1), a lipid peptide that is particularly preferable as the lipid peptide-based gelator is the following compounds formed from a lipid moiety and an amino acid moiety or a peptide moiety. Amino acid abbreviations are as follows: asparagine (Asn), alanine (Ala), glutamine (Gln), glycine (Gly), valine (Val), histidine (His), lysine (Lys), and leucine (Leu)). Myristoyl-His, myristoyl-Lys, myristoyl-Asn, myristoyl-Gln, myristoyl-Gly-His, myristoyl-Gly-Lys, myristoyl-Gly-Asn, myristoyl-Gly-Gln, myristoyl-Gly-Gly-His, myristoyl-Gly-Gly-Lys, myristoyl-Gly-Gly-Asn, myristoyl-Gly-Gly-Gln, myristoyl-Gly-Gly-Gly-His, myristoyl-Gly-Gly-Gly-Lys, myristoyl-Gly-Gly-Gly-Asn, myristoyl-Gly-Gly-Gly-Gln, myristoyl-Gly-Gly-Gly-Gly-His, myristoyl-Gly-Gly-Gly-Gly-Lys, myristoyl-Gly-Gly-Gly-Gly-Asn, myristoyl-Gly-Gly-Gly-Gly-Gin, myristoyl-His, myristoyl-Lys, myristoyl-Asn, myristoyl-Gln, myristoyl-Ala-His, myristoyl-Ala-Lys, myristoyl-Ala-Asn, myristoyl-Ala-Gln, myristoyl-Ala-Ala-His, myristoyl-Ala-Ala-Lys, myristoyl-Ala-Ala-Asn, myristoyl-Ala-Ala-Gln, myristoyl-Ala-Ala-Ala-His, myristoyl-Ala-Ala-Ala-Lys, myristoyl-Ala-Ala-Ala-Asn, myristoyl-Ala-Ala-Ala-Gln, myristoyl-Ala-Ala-Ala-Ala-His, myristoyl-Ala-Ala-Ala-Ala-Lys, myristoyl-Ala-Ala-Ala-Ala-Asn, myristoyl-Ala-Ala-Ala-Ala-Gln, myristoyl-His, myristoyl-Lys, myristoyl-Asn, myristoyl-Gln, myristoyl-Val-His, myristoyl-Val-Lys, myristoyl-Val-Asn, myristoyl-Val-Gln, myristoyl-Val-Val-His, myristoyl-Val-Val-Lys, myristoyl-Val-Val-Asn, myristoyl-Val-Val-Gin, myristoyl-Val-Val-Val-His, myristoyl-Val-Val-Val-Lys, myristoyl-Val-Val-Val-Asn, myristoyl-Val-Val-Val-Gln, myristoyl-Val-Val-Val-Val-His, myristoyl-Val-Val-Val-Val-Lys, myristoyl-Val-Val-Val-Val-Asn, myristoyl-Val-Val-Val-Val-Gln, myristoyl-His, myristoyl-Lys, myristoyl-Asn, myristoyl-Gln, myristoyl-Leu-His, myristoyl-Leu-Lys, myristoyl-Leu-Asn, myristoyl-Leu-Gln, myristoyl-Leu-Leu-His, myristoyl-Leu-Leu-Lys, myristoyl-Leu-Leu-Asn, myristoyl-Leu-Leu-Gln, myristoyl-Leu-Leu-Leu-His, myristoyl-Leu-Leu-Leu-Lys, myristoyl-Leu-Leu-Leu-Asn, myristoyl-Leu-Leu-Leu-Gln, myristoyl-Leu-Leu-Leu-Leu-His, myristoyl-Leu-Leu-Leu-Leu-Lys, myristoyl-Leu-Leu-Leu-Leu-Asn, myristoyl-Leu-Leu-Leu-Leu-Gln; palmitoyl His, palmitoyl Lys, palmitoyl Asn, palmitoyl Gln, palmitoyl Gly-His, palmitoyl Gly-Lys, palmitoyl Gly-Asn, palmitoyl Gly-Gln, palmitoyl Gly-Gly-His, palmitoyl Gly-Gly-Lys, palmitoyl Gly-Gly-Asn, palmitoyl Gly-Gly-Gln, palmitoyl Gly-Gly-Gly-His, palmitoyl Gly-Gly-Gly-Lys, palmitoyl Gly-Gly-Gly-Asn, palmitoyl Gly-Gly-Gly-Gln, palmitoyl Gly-Gly-Gly-Gly-His, palmitoyl Gly-Gly-Gly-Gly-Lys, palmitoyl Gly-Gly-Gly-Gly-Asn, palmitoyl Gly-Gly-Gly-Gly-Gln, palmitoyl His, palmitoyl Lys, palmitoyl Asn, palmitoyl Gln, palmitoyl Ala-His, palmitoyl Ala-Lys, palmitoyl Ala-Asn, palmitoyl Ala-Gln, palmitoyl Ala-Ala-His, palmitoyl Ala-Ala-Lys, palmitoyl Ala-Ala-Asn, palmitoyl Ala-Ala-Gln, palmitoyl Ala-Ala-Ala-His, palmitoyl Ala-Ala-Ala-Lys, palmitoyl Ala-Ala-Ala-Asn, palmitoyl Ala-Ala-Ala-Gln, palmitoyl Ala-Ala-Ala-Ala-His, palmitoyl Ala-Ala-Ala-Ala-Lys, palmitoyl Ala-Ala-Ala-Ala-Asn, palmitoyl Ala-Ala-Ala-Ala-Gln, palmitoyl His, palmitoyl Lys, palmitoyl Asn, palmitoyl Gln, palmitoyl Val-His, palmitoyl Val-Lys, palmitoyl Val-Asn, palmitoyl Val-Gln, palmitoyl Val-Val-His, palmitoyl Val-Val-Lys, palmitoyl Val-Val-Asn, palmitoyl Val-Val-Gln, palmitoyl Val-Val-Val-His, palmitoyl Val-Val-Val-Lys, palmitoyl Val-Val-Val-Asn, palmitoyl Val-Val-Val-Gln, palmitoyl Val-Val-Val-Val-His, palmitoyl Val-Val-Val-Val-Lys, palmitoyl Val-Val-Val-Val-Asn, palmitoyl Val-Val-Val-Val-Gln, palmitoyl His, palmitoyl Lys, palmitoyl Asn, palmitoyl Gln, palmitoyl Leu-His, palmitoyl Leu-Lys, palmitoyl Leu-Asn, palmitoyl Leu-Gln, palmitoyl Leu-Leu-His, palmitoyl Leu-Leu-Lys, palmitoyl Leu-Leu-Asn, palmitoyl Leu-Leu-Gln, palmitoyl Leu-Leu-Leu-His, palmitoyl Leu-Leu-Leu-Lys, palmitoyl Leu-Leu-Leu-Asn, palmitoyl Leu-Leu-Leu-Gln, palmitoyl Leu-Leu-Leu-Leu-His, palmitoyl Leu-Leu-Leu-Leu-Lys, palmitoyl Leu-Leu-Leu-Leu-Asn, palmitoyl Leu-Leu-Leu-Leu-Gln; stearoyl His, stearoyl Lys, stearoyl Asn, stearoyl Gln, stearoyl Gly-His, stearoyl Gly-Lys, stearoyl Gly-Asn, stearoyl Gly-Gln, stearoyl Gly-Gly-His, stearoyl Gly-Gly-Lys, stearoyl Gly-Gly-Asn, stearoyl Gly-Gly-Gln, stearoyl Gly-Gly-Gly-His, stearoyl Gly-Gly-Gly-Lys, stearoyl Gly-Gly-Gly-Asn, stearoyl Gly-Gly-Gly-Gln, stearoyl Gly-Gly-Gly-Gly-His, stearoyl Gly-Gly-Gly-Gly-Lys, stearoyl Gly-Gly-Gly-Gly-Asn, stearoyl Gly-Gly-Gly-Gly-Gln, stearoyl His, stearoyl Lys, stearoyl Asn, stearoyl Gln, stearoyl Ala-His, stearoyl Ala-Lys, stearoyl Ala-Asn, stearoyl Ala-Gln, stearoyl Ala-Ala-His, stearoyl Ala-Ala-Lys, stearoyl Ala-Ala-Asn, stearoyl Ala-Ala-Gln, stearoyl Ala-Ala-Ala-His, stearoyl Ala-Ala-Ala-Lys, stearoyl Ala-Ala-Ala-Asn, stearoyl Ala-Ala-Ala-Gln, stearoyl Ala-Ala-Ala-Ala-His, stearoyl Ala-Ala-Ala-Ala-Lys, stearoyl Ala-Ala-Ala-Ala-Asn, stearoyl Ala-Ala-Ala-Ala-Gln, stearoyl His, stearoyl Lys, stearoyl Asn, stearoyl Gln, stearoyl Val-His, stearoyl Val-Lys, stearoyl Val-Asn, stearoyl Val-Gln, stearoyl Val-Val-His, stearoyl Val-Val-Lys, stearoyl Val-Val-Asn, stearoyl Val-Val-Gln, stearoyl Val-Val-Val-His, stearoyl Val-Val-Val-Lys, stearoyl Val-Val-Val-Asn, stearoyl Val-Val-Val-Gln, stearoyl Val-Val-Val-Val-His, stearoyl Val-Val-Val-Val-Lys, stearoyl Val-Val-Val-Val-Asn, stearoyl Val-Val-Val-Val-Gln, stearoyl His, stearoyl Lys, stearoyl Asn, stearoyl Gln, stearoyl Leu-His, stearoyl Leu-Lys, stearoyl Leu-Asn, stearoyl Leu-Gln, stearoyl Leu-Leu-His, stearoyl Leu-Leu-Lys, stearoyl Leu-Leu-Asn, stearoyl Leu-Leu-Gln, stearoyl Leu-Leu-Leu-His, stearoyl Leu-Leu-Leu-Lys, stearoyl Leu-Leu-Leu-Asn, stearoyl Leu-Leu-Leu-Gln, stearoyl Leu-Leu-Leu-Leu-His, stearoyl Leu-Leu-Leu-Leu-Lys, stearoyl Leu-Leu-Leu-Leu-Asn, and stearoyl Leu-Leu-Leu-Leu-Gln.

Most preferable examples thereof include myristoyl-HiS, myristoyl-Gly-His, myristoyl-Gly-Gly-His, myristoyl-Gly-Gly-Gly-His, myristoyl-Gly-Gly-Gly-Gly-His, palmitoyl-His, palmitoyl-Gly-His, palmitoyl-Gly-Gly-His, palmitoyl-Gly-Gly-Gly-His, palmitoyl-Gly-Gly-Gly-Gly-His, stearoyl-His, stearoyl-Gly-His, stearoyl-Gly-Gly-His, stearoyl-Gly-Gly-Gly-His, and stearoyl-Gly-Gly-Gly-Gly-His.

Gel Formation Mechanism

The gel formation mechanism of the lipid peptide-based gelator that is included in the cosmetic or the external skin preparation of the present invention is totally different from the mechanisms of formation of conventional polymer hydrogels. That is to say, a low-molecular lipid peptide that is contained in the lipid peptide-based gelator self-assembles to form a fibrous configuration, and then the fibers form a network structure, resulting in the network structure to enclose water, an alcohol, a polyhydric alcohol, a hydrophobic organic solvent, a hydrophilic organic solvent, or a miscible, mixed solution thereof to form gel.

When the lipid peptide-based gelator of the present invention that contains the low-molecular lipid peptide of Formula (1) or a pharmacologically usable salt thereof is added to water or a hydrophilic solution such as hydrophilic mixed solutions, the peptide moieties in Formula (1) form an intermolecular non-covalent bond via a hydrogen bond, while the lipid moieties in Formula (1) self-assemble via hydrophobical packing, thereby forming a tubular, secondary assembly, namely, fibers.

For reference, a conceptual view of self-assembly and gelation of a low-molecular lipid peptide in a hydrophilic solution is shown in FIG. 1 (however, not all the low-molecular lipid peptides in the present invention necessarily undergo the self-assembly and the gelation shown in FIG. 1). A low-molecular lipid peptide (a) assembles with each other (b) with its lipid moiety that is a hydrophobic moiety arranged inside to form a fiber (c) via self-assembly.

As the lipid peptide-based gelator used to form the fiber, one lipid peptide-based gelator of the present invention may be used or two or more lipid peptide-based gelators of the present invention may be used in combination. Preferable is one or two, and further preferable is one. Using two or more lipid peptide-based gelators of the present invention, a characteristic that is different from that obtained using one lipid peptide-based gelator of the present invention can be expected to be obtained.

The fiber thus formed can adsorb or include a low-molecular compound. When the fiber of the present invention includes the additives described below that are used in a cosmetic or an external skin preparation, such as hydrophobic compounds including vitamin E, these additives are easily dissolved in an aqueous solution, and as a result, both a hydrophilic compound such as vitamin C and a hydrophobic compound such as vitamin E can be dissolved in one aqueous solution. This technique also facilitates dissolution of a preservative that is less prone to dissolve in water, such as methylparaben. Therefore, in production of cosmetics or external skin preparations, a hydrophobic organic solvent that is used to dissolve a hydrophobic compound can be partly replaced by water, a low-molecular alcohol, or a similar alternative, that is safer to the human bodies.

A gel that is formed with fibers including a low-molecular compound can have a so-called sustained release ability to gradually release the low-molecular compound when applied on the skin and the hair. Therefore, the moisturizing effect and similar effects of cosmetics, and the drug efficacy and similar effects of external skin preparations, for example, can be sustained.

The fiber that is formed in a hydrophilic solution forms a three-dimensional network structure (see (d) in FIG. 1, for example), and then a bond is formed between the peptide moiety on the surface of the fiber and the hydrophilic solution to cause swelling. The swelling leads to the entire hydrophilic solution to gel.

When added to a hydrophobic solution such as hydrophobic solvents and hydrophobic mixed solutions, the lipid peptide-based gelator of the present invention assembles with its peptide moiety in Formula (1) arranged inside and its lipid moiety arranged along the surface via self-assembly to form a tubular, secondary assembly, namely, fibers.

Figure 2:
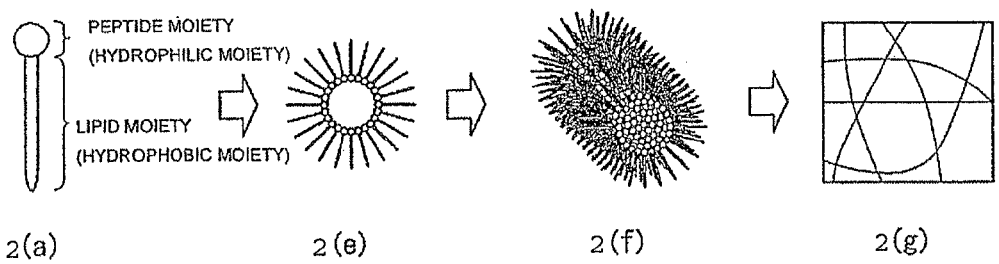
FIGS. 2(a) and 2(e)-2(g) are conceptual views of self-assembly and gelation of a lipid peptide-based gelator in a hydrophobic solution.

For reference, a conceptual view of self-assembly and gelation of a low-molecular lipid peptide in a hydrophobic solution is shown in FIG. 2 (however, not all the low-molecular lipid peptides in the present invention necessarily undergo the self-assembly and the gelation shown in FIG. 1). A lipid peptide molecule (a) assembles with each other (e) with its peptide moiety that is a hydrophilic moiety arranged inside to form a fiber (f) via self-assembly. The fiber that is formed in a mixed solution forms a three-dimensional network structure (see (g) in FIG. 2, for example), and then a bond is formed between the lipid moiety on the surface of the fiber and the mixed solution to cause swelling. The swelling leads to the entire hydrophobic solution to gel.

The lipid peptide-based gelator used in the cosmetic or the external skin preparation of the present invention forms a self-assembly in the mixed solution not only when the mixed solution is gel but also when the mixed solution is a sol and even when the addition amount of the lipid peptide-based gelator is insufficient to achieve gelation, and can maintain the self-assembly after applied on the skin and the hair. Therefore, the cosmetic or the external skin preparation of the present invention is excellent in stretching on the skin surface and the hair surface, is excellent in permeation into the skin and the hair, has the self-assembly adhering to the skin surface and the hair surface so as to hold the solution and an additional ingredient thereon, and causes no dripping. Furthermore, unlike in a cosmetic or an external skin preparation that includes a polymer gelator or an inorganic gelator fine particle, the cosmetic or the external skin preparation of the present invention has an excellent shear property, and therefore is less prone to cause stickiness and crinkles.

Cosmetic or External Skin Preparation

The cosmetic or the external skin preparation of the present invention includes at least one lipid peptide-based gelator.

The concentration of the lipid peptide-based gelator that is included in the cosmetic or the external skin preparation of the present invention is not particularly limited provided that it is effective, and is 0.0001 to 50% (w/v), more preferably 0.0001 to 20% (w/v), and further preferably 0.1 to 5% (w/v), relative to the total volume of the cosmetic or the external skin preparation. When the formulation amount of the lipid peptide-based gelator is less than 0.0001% (w/v), the gelator may not exhibit its effect as a gelator, and when the formulation amount is more than 50% (w/v), long-term storage stability may not be obtained. When the formulation amount is 0.0001 to 50% (w/v), the cosmetic or the external skin preparation can feature excellent stretching on the skin surface and the hair surface, excellent permeation into the skin and the hair, no stickiness or crinkles, and retained storage stability.

The cosmetic or the external skin preparation of the present invention may include, in addition to at least one lipid peptide-based gelator, a water, an alcohol, a polyhydric alcohol, a hydrophilic organic solvent, a hydrophobic organic solvent, or a mixed solution thereof.

Preferable examples of the water include clean water, purified water, hard water, soft water, natural water, deep sea water, electrolyzed alkaline water, electrolyzed acidic water, ionized water, and cluster water.

The alcohol is a monovalent alcohol, and examples thereof include, but are not particularly limited to, $C_{1-6}$ alcohols that dissolve in water at a certain proportion, specifically methanol, ethanol, 2-propanol, isobutanol, and the like, and higher alcohols, specifically oleyl alcohol, phenoxy alcohol, and the like.

The polyhydric alcohol is a divalent or a higher-valent alcohol, and examples thereof include propylene glycol, 1,3-butanediol, 2-ethyl-1,3-hexanediol, glycerin, isopentyldiol, ethylhexanediol, erythrulose, ozonized glycerin, caprylyl glycol, glycol, (C15-18) glycol, (C20-30) glycol, glycerin, diethylene glycol, diglycerin, dithiaoctanediol, DPG, thioglycerin, 1,10-decanediol, decylene glycol, triethylene glycol, thylimethylgydroxy methylcyclohexanol, phytantriol, phenoxypropanediol, 1,2-butanediol, 2,3-butanediol, butylethylpropanediol, 1,2-hexanediol, hexylene glycol, pentylene glycol, methylpropanediol, menthane diol, lauryl glycol, polypropylene glycol, and the like.

The hydrophilic organic solvent means an organic solvent, other than the alcohol and the polyhydric alcohol, that dissolves in the water at a certain proportion. Examples thereof include acetone, dioxanes, ethyl acetate, aqua jojoba oil, and the like.

The hydrophobic organic solvent means an organic solvent, other than the alcohol, that does not freely dissolve in the water. Examples thereof include oils/fats, silicone oils, and ester solvents.

Examples of the oils/fats include castor oil, olive oil, and the like.

Examples of the silicone oils include dimethyl silicone oil, methylphenyl silicone oil, and the like.

Examples of the ester solvent include propylene glycol alginic acid ester, ethyl acetate, diheptylundecyl adipate, acetylated lanolin, isostearyl glyceryl, octyldodecyl isostearate, and the like.

A solvent used in the cosmetic or the external skin preparation of the present invention is preferably water, an alcohol, a polyhydric alcohol, a hydrophobic solvent, a hydrophilic solvent, a mixed solution of water and one or more selected from the group consisting of alcohols, polyhydric alcohols, oils/fats, silicone oils, and ester solvents, or a mixed solution of a polyhydric alcohol and one or more selected from the group consisting of alcohols, oils/fats, silicone oils, and ester solvents. Particularly preferable is water or a solution in which an alcohol or a polyhydric alcohol is dissolved in water.

The cosmetic or the external skin preparation of the present invention may include, where appropriate, an additional ingredient such as physiologically active substances and functional substances that are generally formulated in a cosmetic or an external skin preparation. Examples thereof include oily base materials, moisturizers, tactile-feeling enhancers, surfactants, polymers, thickeners and gelators, solvents, propellants, antioxidants, reducing agents, oxidizing agents, preservatives, antimicrobial agents, antiseptics, chelating agents, pH-adjusting agents, acids, alkalis, powders, inorganic salts, ultraviolet absorbers, skin-brightening agents, vitamins and derivatives thereof, hair growth-promoting agents, blood circulation-promoters, stimulating agents, hormones, anti-wrinkle agents, anti-aging agents, tightening agents, cool-feeling agents, warm-feeling agents, wound-healing promoters, abirritants, analgesics, cell activators, plant, animal, and microbial extracts, antipruritics, keratin-exfoliating/dissolving agents, antiperspirants, refrigerants, styptics, enzymes, nucleic acids, perfumes, coloring agents, colorants, dyes, pigments, antiphlogistics, anti-inflammatory agents, anti-asthmatic agents, drugs for chronic obstructive pulmonary diseases, antiallergic agents, immunomodulators, anti-infective agents, antifungal agents, and the like.

These additional ingredients are exemplified below. Preferable examples of the oily base materials include higher (polyhydric) alcohols such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diols; aralkyl alcohols such as benzyl alcohol, and derivatives thereof, higher fatty acids such as lauric acid, myristic acid, palmitic acid, stearic acid, isostearic acid, behenic acid, undecylene acid, 12-hydroxystearic acid, palmitoleic acid, oleic acid, linoleic acid, linolenic acid, erucic acid, docosahexaenoic acid, eicosapentaenoic acid, isohexadecanoic acid, anteisohenicosanoic acid, branched long-chain fatty acids, dimer acids, and hydrogenated dimer acids, and metallic soaps thereof such as aluminum salts thereof, calcium salts thereof, magnesium salts thereof, zinc salts thereof, potassium salts thereof, and sodium salts thereof, and nitrogen-containing derivatives thereof such as amides thereof; hydrocarbons such as liquid paraffin (mineral oil), heavy liquid isoparaffin, light liquid isoparaffin, α-olefin oligomers, polyisobutene, hydrogenated polyisobutene, polybutene, squalane, olive squalane, squalene, petrolatum, and solid paraffin; waxes such as candelilla wax, carnauba wax, rice wax, Japan wax, beeswax, montan wax, ozokerite, ceresin, paraffin wax, microcrystalline wax, petrolatum, Fischer-Tropsch Wax, polyethylene wax, and ethylene-propylene copolymers; vegetable oils such as coconut oil, palm oil, palm kernel oil, safflower oil, olive oil, castor oil, avocado oil, sesame seed oil, tea oil, evening primrose oil, wheat germ oil, macadamia seed oil, hazelnut oil, kukui nut oil, rose hip oil, meadowfoam oil, persic oil; tea tree oil, mint oil, maize oil, rape oil, sunflower oil, wheat germ oil, linseed oil, cottonseed oil, soybean oil, peanut oil, rice bran oil, cocoa butter, shea butter, hydrogenated coconut oil, hydrogenated castor oil, jojoba oil, and hydrogenated jojoba oil; animal oils/fats such as beef tallow, milk fat, horse fat, egg-yolk oil, mink oil, and turtle oil; animal waxes such as spermaceti, lanolin, and orange roughy oil; lanolins such as liquid lanolin, reduced lanolin, adsorption-purified lanolin, acetylated lanolin, acetylated liquid lanolin, hydroxylated lanolin, polyoxyethylene lanolin, lanolin fatty acid, hard lanolin fatty acid, lanolin alcohol, acetylated lanolin alcohol, and acetylated (cetyl/lanolyl) ester; phospholipids such as lecithin, phosphatidylcholine, phosphatidylethanolamine, phosphatidylserine, phosphatidylglycerol, phosphatidylinositol, sphingophospholipids including sphingomyelin, phosphatidic acid, and lysolecithin; phospholipid derivatives such as hydrogenated soybean phospholipid, partially hydrogenated soybean phospholipid, hydrogenated egg-yolk phospholipid, and partially hydrogenated egg-yolk phospholipid; sterols such as cholesterol, dihydrocholesterol, lanosterol, dihydrolanosterol, phytosterol, and cholic acid; sapogenins; saponins; sterol esters such as cholesteryl acetate, cholesteryl nonanoate, cholesteryl stearate, cholesteryl isostearate, cholesteryl oleate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, acyl sarcosine alkyl esters including isopropyl N-lauroyl sarcosinate, cholesteryl 12-hydroxystearate, cholesteryl macadamiate, phytosteryl macadamiate, phytosteryl isostearate, soft lanolin fatty acid cholesteryl ester, hard lanolin fatty acid cholesteryl ester, branched long-chain fatty acid cholesteryl esters, and long-chain α-hydroxy fatty acid cholesteryl esters; lipid complexes such as phospholipid-cholesterol complexes and phospholipid-phytosterol complexes; monoalcohol carboxylic acid esters such as octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, octyldodecyl lanolate, hexyldecyl dimethyloctanoate, octyldodecyl erucate, hydrogenated castor oil isostearate, ethyl oleate, ethyl avocadate, isopropyl myristate, isopropyl palmitate, octyl palmitate, isopropyl isostearate, isopropyl lanolate, diethyl sebacate, diisopropyl sebacate, dioctyl sebacate, diisopropyl adipate, dibutyloctyl sebacate, diisobutyl adipate, dioctyl succinate, and triethyl citrate; oxyacid esters such as cetyl lactate, diisostearyl malate, and hydrogenated castor oil monoisostearate; polyhydric alcohol fatty acid esters such as glyceryl trioctanoate, glyceryl trioleate, glyceryl triisostearate, glyceryl diisostearate, caprylic/capric triglyceride, caprylic/capric/myristic/stearic triglyceride, hydrogenated rosin triglyceride (hydrogenated ester gum), rosin triglyceride (ester gum), glyceryl behenate eicosanedioate, trimethylolpropane trioctanoate, trimethylolpropane triisostearate, neopentyl glycol dioctanoate, neopentyl glycol dicaprate, 2-butyl-2-ethyl-1,3-propanediol dioctanoate, propylene glycol dioleate, pentaerythrityl tetraoctanoate, hydrogenated rosin pentaerythrityl ester, ditrimethylolpropane triethylhexanoate, ditrimethylolpropane isostearate/sebacate, pentaerythrityl triethylhexanoate, dipentaerythrityl hydroxystearate/stearate/resinate, diglyceryl diisostearate, polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethylene glycol distearate), 3-methyl-1,5-pentanediol dineopentanoate, and 2,4-diethyl-1,5-pentanediol dineopentanoate; dimer acid derivatives or dimer diol derivatives such as diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensates, hydrogenated castor oil dimer dilinoleate, and hydroxyalkyl dimer dilinoleyl ether; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamide (cocamide methyl MEA); silicones such as dimethicone (dimethylpolysiloxane), highly-polymerized dimethicone (highly-polymerized dimethylpolysiloxane), cyclomethicone (cyclic dimethylsiloxane, decamethylcyclopentasiloxane), phenyl trimethicone, diphenyl dimethicone, phenyl dimethicone, stearoxypropyldimethylamine, (aminoethylaminopropyl methicone/dimethicone) copolymer, dimethiconol, dimethiconol crosspolymer, silicone resins, silicone rubber, amino-modified silicones including aminopropyl dimethicone and amodimethicone, cation-modified silicones, polyether-modified silicones including dimethicone copolyols, polyglycerin-modified silicones, sugar-modified silicones, carboxylic acid-modified silicones, phosphoric acid-modified silicones, sulfuric acid-modified silicones, alkyl-modified silicones, fatty acid-modified silicones, alkyl ether-modified silicones, amino acid-modified silicones, peptide-modified silicones, fluorine-modified silicones, cation-modified and polyether-modified silicones, amino-modified and polyether-modified silicones, alkyl-modified and polyether-modified silicones, and polysiloxane-oxyalkylene copolymers; and fluorine oils such as perfluorodecane, perfluorooctane, and perfluoropolyether.

Preferable examples of the moisturizers and the tactile-feeling enhancers include polyols and polymers thereof such as glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymers; glycol alkyl ethers such as diethylene glycol monoethyl ether (ethoxydiglycol), ethylene glycol monoethyl ether, ethylene glycol monobutyl ether, and diethylene glycol dibutyl ether; water-soluble esters such as polyglyceryl-10 (eicosanedioate/tetradecanedioate) and polyglyceryl-10 tetradecanedioate; sugar alcohols such as sorbitol, xylitol, erythritol, mannitol, and maltitol; sugars and derivatives thereof such as glucose, fructose, galactose, mannose, threose, xylose, arabinose, fucose, ribose, deoxyribose, maltose, trehalose, lactose, raffinose, gluconic acid, glucuronic acid, cyclodextrins (α-, β-, and γ-cyclodextrins, and modified cyclodextrins such as maltosyl cyclodextrin and hydroxyalkyl cyclodextrin), β-glucan, chitin, chitosan, heparin and heparin derivatives, pectin, arabinogalactan, dextrin, dextran, glycogen, ethyl glucoside, poly(glucosylethyl methacrylate), and (glucosylethyl methacrylate) copolymer; hyaluronic acid and sodium hyaluronate; sodium chondroitin sulfate; mucoitin sulfate, charonin sulfate, kerato sulfate, and dennatan sulfate; *Tremella fuciformis* extract and *Tremella fuciformis* polysaccharide; fucoidan; tuberose polysaccharide and natural polysaccharides; organic acids such as citric acid, tartaric acid, and lactic acid, and salts thereof; urea and derivatives thereof; 2-pyrrolidone-5-carboxylic acid, and salts thereof including a sodium salt thereof; amino acids such as betaine (trimethylglycine), praline, hydroxyproline, arginine, lysine, serine, glycine, alanine, phenylalanine, tyrosine, β-alanine, threonine, glutamic acid, glutamine, asparagine, aspartic acid, cysteine, cysteine, methionine, leucine, isoleucine, valine, tryptophan, histidine, and taurine, and salts thereof; protein peptides, and derivative thereof, such as collagen, fish collagen, atelocollagen, gelatin, elastin, peptides derived from decomposed collagen, hydrolyzed collagen, hydroxypropylammonium chloride hydrolyzed collagen, peptides derived from decomposed elastin, peptides derived from decomposed keratin, hydrolyzed keratin, peptides derived from decomposed conchiolin, hydrolyzed conchiolin, peptides derived from decomposed silk protein, hydrolyzed silk, sodium lauroyl hydrolyzed silk, peptides derived from decomposed soy protein, peptides derived from decomposed wheat protein, hydrolyzed wheat protein, peptides derived from decomposed casein, and acylated peptides; acylated peptides such as palmitoyl oligopeptide, palmitoyl pentapeptide, and palmitoyl tetrapeptide; silylated peptides; a culture medium of lactic acid bacteria, a yeast extract solution, an eggshell membrane protein, bovine submaxillary mucin, hypotaurine, sesame lignan glycoside, glutathione, albumin, and whey; choline chloride and phosphoryl choline; and animal and plant extract components such as a placenta extract solution, elastin, collagen, aloe extract, *Hamamelis virginiana* water, *Luffa cylindrica* water, *Chamomilla recutita* extract, licorice extract, *Symphytum officinale* extract, silk extract, *Rosa roxburghii* extract, *Achillea millefolium* extract, *Eucalyptus globulus* extract, and *Melilotus officinalis* extract, and ceramides such as natural ceramides (type 1, 2, 3, 4, 5, and 6), hydroxyceramide, pseudoceramide, sphingoglycolipid, ceramide-containing extracts, and glucosylceramide-containing extracts.

Preferable examples of the surfactants include anionic surfactants, nonionic surfactants, cationic surfactants, amphoteric surfactants, polymer surfactants, and the like. Preferable examples of the surfactants are exemplified below. Preferable examples of the anionic surfactants include fatty acid salts such as potassium laurate and potassium myristate; alkyl sulfuric acid ester salts such as sodium lauryl sulfate, triethanolamine lauryl sulfate, and ammonium lauryl sulfate; polyoxyethylene alkyl sulfates such as sodium laureth sulfate and triethanolamine laureth sulfate; acyl N-methyl amino acid salts such as sodium cocoyl methyl taurate, potassium cocoyl methyl taurate, sodium lauroyl methyl taurate, sodium myristoyl methyl taurate, sodium lauroyl methylalaninate, sodium lauroyl sarcosinate, triethanolamine lauroyl sarcosinate, and sodium lauroyl glutamate methylalaninate; acylamino acid salts such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates such as sodium laureth acetate; succinic acid ester salts such as sodium lauroyl monoethanolamide succinate; fatty acid alkanolamide ether carboxylates; acyl lactates; polyoxyethylene fatty amine sulfates; fatty acid alkanolamide sulfates; fatty acid glyceride sulfates such as glycerin hydrogenated coconut oil fatty acid sulfate sodium salt; alkylbenzene polyoxyethylene sulfates; olefin sulfonates such as sodium α-olefin sulfonate; alkyl sulfosuccinates such as disodium lauryl sulfosuccinate and sodium dioctyl sulfosuccinate; alkyl ether sulfosuccinates such as disodium laureth sulfosuccinate, sodium monolauroyl monoethanolamide polyoxyethylene sulfosuccinate, and sodium lauryl polypropylene glycol sulfosuccinate; alkylbenzene sulfonates such as sodium tetradecylbenzene sulfonate and triethanolamine tetradecylbenzene sulfonate; alkyl naphthalene sulfonates; alkane sulfonates; α-sulfofatty acid methyl ester salts; acyl isethionates; alkyl glycidyl ether sulfonates; alkyl sulfoacetates; alkyl ether phosphoric acid ester salts such as sodium laureth phosphate, sodium dilaureth phosphate, sodium trilaureth phosphate, and sodium monooreth phosphate; alkyl phosphoric acid ester salts such as potassium lauryl phosphate; sodium caseinate; alkyl aryl ether phosphates; fatty amide ether phosphates; phospholipids such as phosphatidylglycerol, phosphatidylinositol, and phosphatidic acid; silicone anionic surfactants such as carboxylic acid-modified silicones, phosphoric acid-modified silicones, and sulfuric acid-modified silicones; and the like. Preferable examples of the nonionic surfactants include polyoxyethylene alkyl ethers with various numbers of polyoxyethylenes such as laureths (polyoxyethylene lauryl ethers), ceteths (polyoxyethylene cetyl ethers), steareths (polyoxyethylene stearyl ethers), beheneths (polyoxyethylene behenyl ethers), isosteareths (polyoxyethylene isostearyl ethers), and octyldodeceths (polyoxyethylene octyldodecyl ethers); polyoxyethylene alkyl phenyl ethers; castor oil derivatives and hydrogenated castor oil derivatives such as polyoxyethylene hydrogenated castor oil, polyoxyethylene castor oil, polyoxyethylene hydrogenated castor oil monoisostearate, polyoxyethylene hydrogenated castor oil triisostearate, polyoxyethylene hydrogenated castor oil monopyroglutamate monoisostearate diester, and polyoxyethylene hydrogenated castor oil maleate; polyoxyethylene phytosterol; polyoxyethylene cholesterol; polyoxyethylene cholestanol; polyoxyethylene lanolin; polyoxyethylene reduced lanolin; polyoxyethylene-polyoxypropylene alkyl ethers such as polyoxyethylene-polyoxypropylene cetyl ether, polyoxyethylene-polyoxypropylene 2-decyltetradecyl ether, polyoxyethylene-polyoxypropylene monobutyl ether, polyoxyethylene-polyoxypropylene hydrogenated lanolin, and polyoxyethylene-polyoxypropylene glycerin ether; polyoxyethylene-polyoxypropylene glycol; (poly)glycerin polyoxypropylene glycols such as PPG-9 diglyceryl; glycerin fatty acid partial esters such as glyceryl stearate, glyceryl isostearate, glyceryl palmitate, glyceryl myristate, glyceryl oleate, glyceryl cocoate, glycerin mono-cottonseed oil fatty acid ester, glycerin monoerucate, glycerin sesquioleate, glycerin α,α'-oleate pyroglutamate, and glycerin monostearate malate; polyglycerin fatty acid esters such as polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, polyglyceryl-6 distearate, polyglyceryl-10 distearate, polyglyceryl-2 tristearate, polyglyceryl-10 decastearate, polyglyceryl-2 isostearate, polyglyceryl-3 isostearate, polyglyceryl-4 isostearate, polyglyceryl-5 isostearate, polyglyceryl-6 isostearate, polyglyceryl-8 isostearate, polyglyceryl-10 isostearate, polyglyceryl-2 diisostearate (diglyceryl diisostearate), polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2 oleate, polyglyceryl-3 oleate, polyglyceryl-4 oleate, polyglyceryl-5 oleate, polyglyceryl-6 oleate, polyglyceryl-8 oleate, polyglyceryl-10 oleate, polyglyceryl-6 dioleate, polyglyceryl-2 trioleate, and polyglyceryl-10 decaoleate; ethylene glycol mono-fatty acid esters such as ethylene glycol monostearate; propylene glycol mono-fatty acid esters such as propylene glycol monostearate; pentaerythritol fatty acid partial esters; sorbitol fatty acid partial esters; maltitol fatty acid partial esters; maltitol ether; sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, sorbitan penta-2-ethylhexylate diglycerol, and sorbitan tetra-2-ethylhexylate diglycerol; sugar derivative partial esters such as sucrose fatty acid esters, methyl glucoside fatty acid esters, and trehalose undecylenoate; alkyl glucosides such as caprylyl glucoside; alkyl polyglycosides; lanolin alcohol; reduced lanolin; polyoxyethylene fatty acid monoesters and polyoxyethylene fatty acid diesters such as polyoxyethylene distearate, polyethylene glycol diisostearate, polyoxyethylene monooleate, and polyoxyethylene dioleate; polyoxyethylene-propylene glycol fatty acid esters; polyoxyethylene glycerin fatty acid esters such as polyoxyethylene monooleates including polyoxyethylene glycerin monostearate, polyoxyethylene glycerin monoisostearate, and polyoxyethylene glycerin triisostearate; polyoxyethylene sorbitan fatty acid esters such as polyoxyethylene sorbitan monooleate, polyoxyethylene sorbitan monostearate, polyoxyethylene sorbitan monooleate, and polyoxyethylene sorbitan tetraoleate; polyoxyethylene sorbitol fatty acid esters such as polyoxyethylene sorbitol monolaurate, polyoxyethylene sorbitol monooleate, polyoxyethylene sorbitol pentaoleate, and polyoxyethylene sorbitol monostearate; polyoxyethylene methyl glucoside fatty acid esters; polyoxyethylene alkyl ether fatty acid esters; polyoxyethylene-modified animal and vegetable oils/fats such as polyoxyethylene sorbitol beeswax; alkyl glyceryl ethers such as isostearyl glyceryl ether, chimyl alcohol, selachyl alcohol, and batyl alcohol; polyhydric alcohol alkyl ethers; polyoxyethylene alkylamines; tetrapolyoxyethylene/tetrapolyoxypropylene-ethylenediamine condensates; natural surfactants such as saponins and sophorolipid; polyoxyethylene fatty acid amides; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamide (cocamide methyl MEA); alkyl dimethylamine oxides such as lauramine oxide, cocamine oxide, stearamine oxide, and behenamine oxide; alkyl ethoxy dimethylamine oxides; polyoxyethylene alkyl mercaptans; silicone nonionic surfactants such as polyether-modified silicones including dimethicone copolyols, polysiloxane-oxyalkylene copolymers, polyglycerin-modified silicones, and sugar-modified silicones; and the like. Preferable examples of the cationic surfactants include alkyl trimethylammonium chlorides such as behentrimonium chloride, steartrimoniurn chloride, cetrimonium chloride, and lauryltrimonium chloride; alkyl trimethylammonium bromides such as stearyltrimonium bromide; dialkyl dimethylammonium chlorides such as distearyldimonium chloride and dicocodimonium chloride; fatty acid amide amines such as stearamide propyldimethylamine and stearamide ethyldiethylamine, and salts thereof; alkyl ether amines such as stearoxypropyldimethylamine, and salts and quaternary salts thereof; fatty acid amide quaternary ammonium salts such as branched long-chain fatty acid (12 to 31) aminopropylethyldimethylammonium ethyl sulfates and lanolin aminopropylethyldimethylammonium ethyl sulfate; polyoxyethylene alkylamines, and salts and quaternary salts thereof; alkylamine salts; fatty acid amide guanidium salts; alkyl ether ammonium salts; alkyl trialkylene glycol ammonium salts; benzalkonium salts; benzethonium salts; pyridinium salts such as cetylpyridinium chloride; imidazolinium salts; alkyl isoquinolinium salts; dialkyl morpholinium salts; polyamine fatty acid derivatives; silicone cationic surfactants such as amino-modified silicones including aminopropyl dimethicone and amodimethicone, cation-modified silicones, cation-modified and polyether-modified silicones, and amino-modified and polyether-modified silicones; and the like. Preferable examples of the amphoteric surfactants include N-alkyl-N,N-dimethylamino acid betaines such as lauryl betaine (lauryl dimethylaminoacetic acid betaine); fatty acid amide alkyl-N,N-dimethylamino acid betaines such as cocamide propyl betaine and lauramide propyl betaine; imidazoline-type betaines such as sodium cocoamphoacetate and sodium lauroamphoacetate; alkyl sulfobetaines such as alkyl dimethyltaurines; sulfuric acid-type betaines such as alkyl dimethylamino ethanol sulfuric acid esters; phosphoric acid-type betaines such as alkyl dimethylamino ethanol phosphoric acid esters; phospholipids such as phosphatidylcholine, phosphatidylethanolamine, phosphatidylserine, sphingophospholipids including sphingomyelin, lysolecithin, hydrogenated soybean phospholipid, partially hydrogenated soybean phospholipid, hydrogenated egg-yolk phospholipid, partially hydrogenated egg-yolk phospholipid, and hydroxylated lecithin; silicone amphoteric surfactants; and the like. Preferable examples of the polymer surfactants include polyvinyl alcohol, sodium alginate, starch derivatives, gum tragacanth, and acrylic acid-alkyl methacrylate copolymers; and various silicone surfactants.

Preferable examples of the polymers, the thickeners, and the gelators include guar gum, locust bean gum, quince seed, carrageenan, galactan, gum arabic, tara gum, tamarind, furcelleran, karaya gum, *Abelmoschus manihot*, cara gum, gum tragacanth, pectin, pectic acid and salts thereof including a sodium salt thereof, alginic acid and salts thereof including a sodium salt thereof, and mannan; starchs such as rice starch, corn starch, potato starch, and wheat starch; xanthan gum, dextran, succinoglucan, curdlan, hyaluronic acid and salts thereof, xanthan gum, pullulan, gellan gum, chitin, chitosan, agar-agar, brown algae extract, chondroitin sulfate, casein, collagen, gelatin, and albumin; cellulose and derivatives thereof such as methylcellulose, ethylcellulose, hydroxyethylcellulose, hydroxypropylcellulose, hydroxypropylmethylcellulose, carboxymethylcellulose and salts thereof including sodium salts thereof, methylhydroxypropylcellulose, sodium cellulose sulfate, dialkyl dimethylammonium sulfate cellulose, crystalline cellulose, and cellulose powder; starch derivatives such as soluble starch, starch polymers including carboxymethyl starch, methylhydroxypropyl starch, and methyl starch, starch hydroxypropyltrimonium chloride, and aluminum corn starch octenylsuccinate; alginic acid derivatives such as sodium alginate and propylene glycol alginic acid ester; polyvinylpyrrolidone (PVP), polyvinyl alcohol (PVA), vinylpyrrolidone-vinyl alcohol copolymers, and polyvinyl methyl ether; polyethylene glycol, polypropylene glycol, and polyoxyethylene-polyoxypropylene copolymers; amphoteric methacrylic acid ester copolymers such as (methacryloyloxyethylcarboxy betaine/alkyl methacrylate) copolymers and (acrylate/stearyl acrylate/ethylamine oxide methacrylate) copolymers; (dimethicone/vinyl dimethicone) crosspolymer, (alkyl acrylate/diacetone acrylamide) copolymer, and (alkyl acrylate/diacetone acrylamide) copolymer AMP; partially saponified polyvinyl acetate and maleic acid copolymers; vinylpyrrolidone-dialkyl aminoalkyl methacrylate copolymers; acrylic resin alkanolamines; polyesters and water-dispersable polyesters; polyacrylamides; polyacrylic acid ester copolymers such as ethyl polyacrylate, carboxyvinyl polymers, polyacrylic acid and salts thereof including a sodium salt thereof, acrylic acid-methacrylic acid ester copolymers; acrylic acid-alkyl methacrylate copolymers; cationized celluloses such as polyquaternium-10, diallyldimethylammonium chloride-acrylamide copolymers such as polyquaternium-7, acrylic acid-diallyldimethylammonium chloride copolymers such as polyquaternium-22, acrylic acid-diallyldimethylammonium chloride-acrylamide copolymers such as polyquaternium-39, acrylic acid-cationized methacrylic acid ester copolymers, acrylic acid-cationized methacrylic acid amide copolymers, acrylic acid-methyl acrylate-methacrylamide propyltrimethylammonium chloride copolymers such as polyquaternium-47, and methacryloyl chloride choline ester polymers; cationized polysaccharides such as cationized oligosaccharides, cationized dextran, and guar hydroxypropyltrimonium chloride; polyethyleneimines; cationic polymers; polymers of 2-methacryloyloxyethylphosphorylcholine such as polyquaternium-51, and copolymers thereof with butyl methacrylate copolymer and the like; polymer emulsions such as acrylic resin emulsions, ethyl polyacrylate emulsions, polyacrylic alkyl ester emulsions, polyvinyl acetate resin emulsions, natural rubber latex, and synthetic latex; nitrocellulose; polyurethanes and various copolymers thereof; various silicones; various silicone copolymers such as acrylic-silicone graft copolymers; various fluorine polymers; 12-hydroxystearic acid and salts thereof; dextrin fatty acid esters such as dextrin palmitate and dextrin myristate; and silicic anhydride, fumed silica (silicic anhydride ultrafine particles), magnesium aluminum silicate, magnesium sodium silicate, metallic soaps, metal dialkyl phosphates, bentonite, hectorite, organo-modified clay mineral, sucrose fatty acid esters, and fructooligosaccharide fatty acid esters. Among them, cellulose and derivatives thereof, alginic acid and salts thereof, polyvinyl alcohol, hyaluronic acid and salts thereof, and collagen are preferable.

Preferable examples of the solvents and the propellants include lower alcohols such as ethanol, 2-propanol (isopropyl alcohol), butanol, and isobutyl alcohol; glycols such as propylene glycol, 1,3-butylene glycol, diethylene glycol, dipropylene glycol, and isopentyldiol; glycol ethers such as diethylene glycol monoethyl ether (ethoxydiglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters such as ethylene glycol monoethyl ether acetate, diethylene glycol monoethyl ether acetate, and propylene glycol monoethyl ether acetate; glycol esters such as diethoxyethyl succinate and ethylene glycol disuccinate; benzyl alcohol, benzyloxyethanol, propylene carbonate, dialkyl carbonate, acetone, ethyl acetate, and N-methylpyrrolidone; toluene; fluorocarbon and next-generation fron; and propellants such as LPG, dimethyl ether, and carbonic acid gas.

Preferable examples of the antioxidants include tocopherol (vitamin E) and tocopherol derivatives such as tocopherol acetate; BHT and BHA; gallic acid derivatives such as propyl gallate; vitamin C (ascorbic acid) and/or derivatives thereof; erythorbic acid and derivatives thereof; sulfites such as sodium sulfite; hydrogen sulfites such as sodium hydrogen sulfite; thiosulfates such as sodium thiosulfate; hydrogen metasulfites; thiotaurine and hypotaurine; and thioglycerol, thiourea, thioglycolic acid, and cysteine hydrochloride.

Preferable examples of the reducing agents include thioglycolic acid, cysteine, cysteamine, and the like.

Preferable examples of the oxidizing agents include a hydrogen peroxide solution, ammonium persulfate, sodium bromate, percarbonic acid, and the like.

Preferable examples of the preservatives, the antimicrobial agents, and the antiseptics include hydroxybenzoic acids and salts and esters thereof such as methylparaben, ethylparaben, propylparaben, and butylparaben; salicylic acid; sodium benzoate; phenoxyethanol; 1,2-diols such as 1,2-pentanediol and 1,2-hexanediol; isothiazolinone derivatives such as methylchloroisothiazolinone and methylisothiazolinone; imidazolinium urea; dehydroacetic acid and salts thereof; phenols; halogenated bisphenols such as triclosan, acid amides, and quaternary ammonium salts; trichlorocarbamide, zinc pyrithione, benzalkonium chloride, benzethonium chloride, sorbic acid, chlorhexidine, chlorhexidine gluconate, halocarban, hexachlorophene, and hinokitiol; phenol and other phenols such as isopropylphenol, cresol, thymol, p-chlorophenol, phenylphenol, and sodium phenylphenolate; and phenylethyl alcohol, photosensitive dyes, antimicrobial zeolite, and a silver ion.

Preferable examples of the chelating agents include edetates (ehylenediamine tetraacetates) such as EDTA, EDTA-Na2, EDTA-Na3, and EDTA-Na4; hydroxyethylethylenediaminetriacetates such as HEDTA-Na3; pentetates (diethylenetriaminepentaacetate); phytic acid; phosphonic acids such as etidronic acid, and salts thereof including sodium salts thereof; sodium oxalate; polyamino acids such as polyaspartic acid and polyglutamic acid; sodium polyphosphate, sodium metaphosphate, and phosphoric acid; and sodium citrate, citric acid, alanine, dihydroxyethylglycine, gluconic acid, ascorbic acid, succinic acid, and tartaric acid.

Preferable examples of the pH-adjusting agents, acids, and alkalis include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propanediol, 2-amino-2-hydroxymethyl-1,3-propanediol, arginine, sodium hydroxide, potassium hydroxide, an aqueous ammonia solution, guanidine carbonate, and ammonium carbonate.

Preferable examples of the powders include inorganic powders of various sizes and shapes such as mica, talc, kaolin, sericite, montmorillonite, kaolinite, mica, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstates, magnesium, zeolite, barium sulfate, calcined calcium sulfate, calcium phosphate, fluorapatite, hydroxyapatite, ceramic powder, bentonite, smectite, clay, mud, metallic soaps (zinc myristate, calcium palmitate, and aluminum stearate, for example), calcium carbonate, red iron oxide, yellow iron oxide, black iron oxide, ultramarine, prussian blue, carbon black, titanium oxide, titanium oxide fine particles and titanium oxide ultrafine particles, zinc oxide, zinc oxide fine particles and zinc oxide ultrafine particles, alumina, silica, fumed silica (silicic anhydride ultrafine particles), titanated mica, fish scale guanine, boron nitride, photochromic pigments, synthetic fluorophlogopite, fine-particle composite powders, gold, and aluminum, and these inorganic powders that are treated with a silicone such as hydrogen silicone and cyclic hydrogen silicone or are otherwise treated with various surface-treating agents such as silane coupling agents and titanium coupling agents to hydrophobize or hydrophilize these inorganic powders; and organic powders, surface-treated organic powders, and organic-inorganic composite powders of various sizes and shapes such as starch, cellulose, nylon powder, polyethylene powder, polymethyl methacrylate powder, polystyrene powder, styrene/acrylate copolymer resin powder, polyester powder, benzoguanamine resin powder, polyethylene terephthalate/polymethyl methacrylate-laminated powder, polyethylene terephthalate/aluminum/epoxy-laminated powder, urethane powder, silicone powder, and Teflon (registered trademark) powder.

Preferable examples of the inorganic salts include sodium chloride-containing salts such as common salt, regular salt, rock salt, sea salt, and natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as mono-, di-, and trisodium phosphates, potassium phosphates, calcium phosphates, and magnesium phosphates.

Preferable examples of the ultraviolet absorbers include benzoate-based ultraviolet absorbers such as p-aminobenzoic acid, p-aminobenzoic acid monoglycerin ester, N,N-dipropoxy p-aminobenzoic acid ethyl ester, N,N-diethoxy p-aminobenzoic acid ethyl ester, N,N-dimethyl p-aminobenzoic acid ethyl ester, N,N-dimethyl p-aminobenzoic acid butyl ester, and N,N-dimethyl p-aminobenzoic acid ethyl ester; anthranilate-based ultraviolet absorbers such as homomenthyl-N-acetylanthranilate; salicylate-based ultraviolet absorbers such as salicylic acid and a sodium salt thereof, amyl salicylate, menthyl salicylate, homomenthyl salicylate, octyl salicylate, phenyl salicylate, benzyl salicylate, and p-isopropanolphenyl salicylate; cinnamate-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethylhexyl p-methoxy cinnamate (octyl p-methoxy cinnamate), 2-ethoxyethyl-p-methoxy cinnamate (cinoxate), cyclohexyl-p-methoxy cinnamate, ethyl-α-cyano-β-phenyl cinnamate, 2-ethylhexyl α-cyano-β-phenyl cinnamate (octocrylene), glyceryl mono-2-ethylhexanoyl-di-p-methoxy cinnamate, and ferulic acid and derivatives thereof; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzyliderie)-d,l-camphor and 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenyl)benzotriazole; dibenzalazines; dianisoylmethane; 5-(3,3-dimethyl-2-norbornylidene)-3-pentan-2-one; dibenzoylmethane derivatives such as 4-t-butylmethoxydibenzoylmethane; octyl triazone; urocanic acid, and urocanic acid derivatives such as ethyl urocanate; and 2-(2'-hydroxy-5'-methylphenyl)benzotriazole, 1-(3,4-dimethoxyphenyl)-4,4-dimethyl-1,3-pentanedione, hydantoin derivatives such as 2-ethylhexyl dimethoxybenzylidene dioxoimidazolidine propionate, phenylbenzimidazole sulfonic acid, terephthalylidene dicamphor sulfonic acid, drometrizole trisiloxane, methyl anthranilate, rutin and derivatives thereof, and orizanol and derivatives thereof.

Preferable examples of the skin-brightening agents include hydroquinone glycosides such as arbutin and α-arbutin, and esters thereof; ascorbic acid and ascorbic acid derivatives such as ascorbyl phosphate salts including sodium ascorbyl phosphate and magnesium ascorbyl phosphate, ascorbyl fatty acid esters including ascorbyl tetraisopalmitate, ascorbic acid alkyl ethers including ascorbic acid ethyl ether, ascorbyl glucosides including ascorbyl 2-glucoside and fatty acid esters thereof, ascorbyl sulfurate, and tocopheryl ascorbyl phosphate; and kojic acid, ellagic acid, tranexamic acid and derivatives thereof, ferulic acid and derivatives thereof, placenta extract, glutathione, orizanol, butyl resorcinol, and plant extracts such as oil-soluble *Chamomilla recutita* extract, oil-soluble licorice extract, Seikaryu extract, and *Saxifraga sarmentosa* extract Preferable examples of the vitamins and derivatives thereof include vitamin As such as retinol, retinol acetate, and retinol palmitate; vitamin Bs such as thiamine hydrochloride, thiamine sulfate, riboflavin, riboflavin acetate, pyridoxine hydrochloride, pyridoxine dioctanoate, pyridoxine dipalmitate, flavin adenine dinucleotide, cyanocobalamine, folic acids, nicotinic acids such as nicotinamide and benzyl nicotinate, and cholines; vitamin Cs such as ascorbic acid and salts thereof including a sodium salt thereof; vitamin Ds; vitamin Es such as α-, β-, γ-, and δ-tocopherols; other vitamins such as pantothenic acid and biotin; ascorbic acid derivatives such as ascorbyl phosphate salts including sodium ascorbyl phosphate and magnesium ascorbyl phosphate, ascorbyl fatty acid esters including ascorbyl tetraisopalmitate, ascorbyl stearate, ascorbyl palmitate, and ascorbyl dipalmitate, ascorbic acid alkyl ethers including ascorbic acid ethyl ether, ascorbyl glucosides including ascorbyl 2-glucoside and fatty acid esters thereof, and tocopheryl ascorbyl phosphate; and vitamin derivatives such as tocopherol derivatives including tocopherol nicotinate, tocopherol acetate, tocopherol linoleate, tocopherol ferulate, and tocopherol phosphate, tocotrienol, and other various vitamin derivatives.

Preferable examples of the hair growth-promoting agents, the blood circulation-promoters, and the stimulating agents include plant extracts and tinctures such as *Swertia herb* extract, *Capsicum fiutescens* tincture, ginger tincture, ginger extract, and cantharides tincture; and capsaicin, nonylic acid vanillylamide, zingerone, ichthammol, tannic acid, bomeol, cyclandelate, cinnarizine, tolazoline, acetylcholine, verapamil, cepharanthine, γ-orizanol, vitamin E and derivatives thereof including tocopherol nicotinate and tocopherol acetate, γ-orizanol, nicotinic acid and derivatives thereof including nicotinamide, benzyl nicotinate, inositol hexanicotinate, and nicotinic alcohol, allantoin, Kankoso 301, Kankoso 401, carpronium chloride, pentadecanoic acid monoglyceride, flavanonol derivatives, stigmasterol and stigmastanol and glycosides thereof, and minoxidil.

Preferable examples of the hormones include estradiol, estrone, ethynylestradiol, cortisone, hydrocortisone, prednisone, and the like.

Preferable examples of other substances with drug efficacy such as the anti-wrinkle agents, the anti-aging agents, the tightening agents, the cool-feeling agents, the warm-feeling agents, the wound-healing promoters, the abirritants, the analgesics, and the cell activators include retinols, retinoic acids, and tocopheryl retinoate; lactic acid, glycolic acid, gluconic acid, fruit acid, and salicylic acid and derivatives thereof including glycosides thereof and esters thereof, and α- and β-hydroxy acids and derivatives thereof such as hydroxycapric acid, long-chain α-hydroxy fatty acids, long-chain α-hydroxy fatty acid cholesteryl esters; γ-aminobutyric acid and γ-amino-β-hydroxybutyric acid; carnitine; carnosine; creatine; ceramides and sphingosines; caffeine, xanthine, and the like and derivatives thereof; antioxidizing agents and active oxygen scavengers such as coenzyme Q10, carotin, lycopene, astaxanthin, lutein, α-lipoic acid, colloidal platinum nanoparticles, and fullerenes; catechins; flavones such as quercetin; isoflavones; gallic acid and sugar ester derivatives thereof; polyphenols such as tannin, sesamin, proanthocyanidin, chlorogenic acid, and apple polyphenol; rutin and derivatives thereof including glycosides thereof; hesperidin and derivatives thereof including glycosides thereof; lignan glycoside; licorice extract-related substances such as glabridin, glabrene, liquiritin, and isoliquiritin; lactoferrin; shogaol and gingerol; perfume substances such as menthol and cedrol, and derivatives thereof; capsaicin, vanillin, and the like and derivatives thereof; insect repellents such as diethyltoluamide; and complexes of physiologically active substances and cyclodextrins.

Preferable examples of the plant, animal, and microbial extracts include extracts such as iris extract, *Angelica keiskei* extract, *Thujopsis dolabrata* extract, asparagus extract, avocado extract, *Hydrangea serrata* extract, almond extract, *Althaea officinalis* extract, *Arnica montana* extract, aloe extract, apricot extract, apricot kernel extract, *Gingko biloba* extract, *Artemisia capillaris* flower extract, fennel seed extract, turmeric root extract, oolong tea extract, *Arctostaphylos uva-ursi* leaf extract, *Rosa multiflora* fruit extract, *Echinacea angustifolia* leaf extract, *Isodonis japonicus* extract, *Scutellaria baicalensis* extract, *Phellodendron amurense* bark extract, *Coptis japonica* root extract, *Hordeum vulgare* extract, *Panax ginseng* extract, *Hypericum perforatum* extract, *Lamium album* extract, *Ononis spinosa* extract, *Nasturtium officinale* extract, orange extract, dried sea water residues, seaweed extract, *Persimmon leaf* extract, *Pyracantha fortuneana* extract, hydrolyzed elastin, hydrolyzed wheat powder, hydrolyzed silk, *Pueraria lobata* root extract, *Chamomilla recutita* extract, oil-soluble *Chamomilla recutita* extract, *Daucus carota* sativa extract, *Artemisia capillaris* extract, *Avena fatua* extract, carcade extract, licorice extract, oil-soluble licorice extract, kiwi fruit extract, kiou extract, *Auricularia auricula-judae* extract, *Cinchona succirubra* extract, cucumber extract, *Paulownia tomentosa* leaf extract, guanosine, guava extract, *Sophora angustifolia* extract, *Gardenia florida* extract, *Sasa veitchii* extract, *Sophora angustifolia* extract, walnut extract, chestnut extract, grapefruit extract, *Clematis vitalba* extract, *Oryza sativa* Linne. extract, black sugar extract, black vinegar, *Chlorella vulgaris* extract, *Morus alba* extract, *Gentiana lutea* extract, *Geranium thunbergii* extract, black tea extract, yeast extract, magnolia bark extract, coffee seed extract, *Arctium lappa* root extract, rice extract, fermented rice extract, fermented rice bran extract, rice germ oil, *Symphytum officinale* extract, collagen, *Vaccinium vitis-idaea* extract, *Asarum sieboldi* extract, *Bupleurum falcatum* extract, umbilical extract, saffron extract, salvia extract, *Saponaria officinalis* extract, sasa extract, *Crataegus cuneata* fruit extract, *Bombyx mori* excrementum extract, *Zanthoxylum piperitum* extract, *Corthellus shiitake* extract, *Rehmaimia glutinosa* extract, *Lithosperrnum erythrorhizon* root extract, *Perilla ocymoides* extract, *Tilia cordata* extract, *Spiraea ulmaria* extract, jatoba extract, *Paeonia albiflora* extract, ginger extract, *Acarus calamus* root extract, *Betula Platyphylla Japonica* extract, *Tremella fuciformis* extract, *Equisetum arvense* extract, stevia extract, stevia fermentation product, *Seikaryu* extract, *Hedera helix* extract, *Crataegus oxyacantha* extract, *Sambucus nigra* extract, *Achillea millefolium* extract, *Mentha piperita* extract, sage extract, *Malva sylvestris* extract, *Cnidium officinale* extract, *Swertia* herb extract, *Mortis alba* root extract, *Rheum* extract, soybean extract, *Zizyphus jujuba* extract, thyme extract, dandelion extract, lichen extract, *Camellia sinensis* leaf extract, clove extract, *Imperata cylindrica* extract, *Citrus unshiu* peel extract, tea tree oil, *Rubus suavissimus* extract, *Capsicum frutescens* extract, *Angelica acutiloba* extract, *Calendula officinalis* extract, *Prunus persica* kernel extract, *Citrus aurantium amara* peel extract, *Houttuynia cordata* extract, tomato extract, natto extract, carrot extract, garlic extract, *Rosa canina* extract, hibiscus extract, *Ophiopogon japonicus* root extract, *Nelumbo nucifera* extract, parsley extract, birch extract, honey, *Hamamelis virginiana* extract, *Parietaria officinalis* extract, *Isodonis japonicus* extract, bisabolol, *Chamaecyparis obtusa* extract, *Bifidobacterium* extract, *Eriobotrya japonica* extract, *Tussilago farfara* extract, *Petasites japonicus* flower stalk extract, *Poria cocos* sclerotium extract, *Ruscus aculeatus* extract, grape extract, grape seed extract, propolis, *Luffa cylindrica* extract, safflower extract, peppermint extract, *Tilia miqueliana* extract, *Paeonia suffruticosa* root extract, hops extract, *Rosa rugosa* flower extract, *Pinus sylvestris* cone extract, horse chestnut extract, *Lysichiton camtschatcense* extract, *Sapindus mukurossi* peel extract, *Melissa officinalis* extract, *Nemacystus decipiens* extract, peach extract, *Centaurea cyanus* extract, *Eucalyptus globulus* extract, *Saxifraga sarmentosa* extract, *Citrus junos* extract, lily extract, *Coix lacryma-jobi* seed extract, *Artemisia princeps* extract, lavender extract, green tea extract, egg shell membrane extract, apple extract, rooibos tea extract, *Ganoderma lucidum* extract, lettuce extract, lemon extract, forsythia extract, *Astragalus sinicus* extract, rose extract, rosemary extract, *Anthemis nobilis* extract, royal jelly extract, and *Sanguisorba officinalis* root extract.

Examples of the antipruritics include diphenhydramine hydrochloride, chlorpheniramine maleate, camphor, a substance P inhibitor, and the like.

Examples of the keratin-exfoliating/dissolving agents include salicylic acid, sulfur, resorcin, selenium sulfide, pyridoxine, and the like.

Examples of the antiperspirants include aluminum chlorohydrate, aluminum chloride, zinc oxide, zinc p-phenolsulfonate, and the like.

Examples of the refrigerants include menthol, methyl salicylate, and the like.

Examples of the styptics include citric acid, tartaric acid, lactic acid, aluminum potassium sulfate, tannic acid, and the like.

Examples of the enzymes include superoxide dismutases, catalases, lysozyme chloride, lipases, papain, pancreatin, proteases, and the like.

Preferable examples of the nucleic acids include ribonucleic acid and salts thereof, deoxyribonucleic acid and salts thereof, and adenosine triphosphate disodium.

Preferable examples of the perfumes include synthetic perfumes and natural perfumes such as acetyl cedrene, amylcinnamaldehyde, allylamyl glycolate, β-ionone, Iso E Super, isobutylquinoline, iris oil, irone, indole, ylang-ylang oil, undecanal, undecenal, γ-undecalactone, estragole, eugenol, oakmoss, opoponax resinoid, orange oil, eugenol, aurantiol, galacsolid, carvacrol, L-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-t-butylcyclohexyl acetate, vetiveryl acetate, benzyl acetate, linalyl acetate, isopentyl salicylate, benzyl salicylate, sandalwood oil, santalol, cyclamen aldehyde, cyclopentadecanolide, methyl dihydrojasmonate, dihydromyrcenol, jasmine absolute, Jasmin lactone, cis-jasmone, citral, citronellol, citronellal, cinnamon bark oil, 1,8-cineole, cinnamaldehyde, styrax resinoid, cedarwood oil, cedrene, cedrol, celery seed oil, thyme oil, damascone, damascenone, thymol, tuberose absolute, decanal, decalactone, terpineol, γ-terpinen, triplal, nerol, nonanal, 2,6-nonadienal, nonalactone, patchouli alcohol, vanilla absolute, vanillin, basil oil, patchouli oil, hydroxycitronellal, α-pinene, piperitone, phenethyl alcohol, phenylacetaldehyde, petitgrain oil, hexylcinnamaldehyde, cis-3-hexenol, Peru balsam, vetiver oil, vetiverol, peppermint oil, pepper oil, heliotropin, bergamot oil, benzyl benzoate, bomeol, mil resinoid, musk ketone, methyl nonyl acetaldehyde, γ-methyl ionone, menthol, L-menthol, L-menthone, *Eucalyptus globulus* oil, β-ionone, lime oil, lavender oil, D-limonene, linalool, lyral, lilial, lemon oil, rose absolute, rose oxide, rose oil, rosemary oil, and various essential oils, and various perfume blends.

Preferable examples of the coloring agents, the colorants, the dyes, and the pigments include Japanese cosmetic colors such as Brown No. 201, Black No. 401, Violet No, 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No, 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No, 204, Orange No. 205, Orange No. 206, Orange No. 207, Orange No. 401, Orange No. 402, Orange No. 403, Yellow No. 201, Yellow No. 202-1, Yellow No. 202-2, Yellow No. 203, Yellow No. 204, Yellow No. 205, Yellow No. 4, Yellow No. 401, Yellow No. 402, Yellow No. 403-1, Yellow No. 404, Yellow No. 405, Yellow No. 406, Yellow No. 407, and Yellow No. 5; other acid dyes such as Acid Red No. 14; basic dyes such as Arianor Sienna Brown, Arianor Madder Red, Arianor Steel Blue, and Arianor Straw Yellow; nitro dyes such as HC Yellow No. 2, HC Yellow No. 5, HC Red No. 3, 4-hydoxypropylamino-3-nitrophenol, N,N'-bis(2-hydroxyethyl)-2-nitro-p-phenylenediamine, HC Blue No. 2, and Basic Blue No. 26; disperse dyes; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ochre; inorganic black pigments such as black iron oxide and low-dimensional titanium oxide; inorganic violet pigments such as mango violet and cobalt violet; inorganic green pigments such as chromium oxide, chromium hydroxide, and cobalt titanium oxide; inorganic blue pigments such as ultramarine and prussian blue; pearl pigments such as titanium oxide-coated mica, titanium oxide-coated bismuth oxychloride, titanium oxide-coated talc, colored titanium oxide-coated mica, bismuth oxychloride, and fish scale guanine; metallic powder pigments such as aluminum powder, copper powder, and gold; surface-treated inorganic and metallic powder pigments; organic pigments such as zirconium lake, barium lake, and aluminum lake; surface-treated organic pigments; natural coloring agents and natural dyes such as astaxanthin, anthraquinones including alizarin, anthocyanidine, β-carotin, catenal, capsanthin, chalcone, carthamin, quercetin, crocin, chlorophyll, curcumin, cochineal, naphthoquinones including shikonin, bixin, flavones, betacyanidine, henna, hemoglobin, lycopene, riboflavin, and rutin; oxidation dye intermediates and couplers such as p-phenylenediamine, toluene-2,5-diamine, o-, m-, and p-aminophenols, m-phenylenediamine, 5-amino-2-methyl phenol, resorcin, 1-naphthol, 2,6-diaminopyridine, and the like, and salts thereof; autoxidizable dyes such as indoline; and dihydroxyacetone.

Preferable examples of the antiphlogistics and the anti-inflammatory agents include glycyrrhizic acid and derivatives thereof, glycyrrhetinic acid derivatives, salicylic acid derivatives, hinokitiol, guaiazulene, allantoin, indomethacin, ketoprofen, ibuprofen, diclofenac, loxoprofen, celecoxib, inflixiinab, etanercept, zinc oxide, hydrocortisone acetate, prednisone, diphenidolamine hydrochloride, and chlorpheniramine maleate; and plant extracts such as peach leaf extract and *Artemisia princeps* leaf extract.

Preferable examples of the anti-asthmatic agents, the drugs for chronic obstructive pulmonary disease, the anti-allergic agents, and the immunomodulators include aminophylline, theophyllines, steroids (fluticasone, beclomethasone, and the like), leukotriene antagonists, thromboxane inhibitors, Intal, β2-agonists (formoterol, salmeterol, albuterol, tulobuterol, clenbuterol, epinephrine, and the like), tiotropium, ipratropium, dextromethorphan, dimemorfan, bromhexine, tranilast, ketotifen, azelastine, cetirizine, chlorpheniramine, mequitazine, tacrolimus, cyclosporin, sirolimus, methotrexate, cytokine modulators, interferon, omalizumab, and proteins and antibodies.

Preferable examples of the anti-infective agents and the antifungal agents include oseltamivir, zanamivir, and itraconazole.

Other than these, known cosmetic ingredients, known pharmaceutical ingredients, known food ingredients, and the like such as ingredients described in The Japanese Standards of Cosmetic Ingredients, Japanese Cosmetic Ingredients Codex, Japanese Cosmetic Labeling Name list issued by Japan Cosmetic Industry Association, INCI dictionary (The International Cosmetic Ingredient Dictionary and Handbook), Japanese Standards of Quasi-drug Ingredients, Japanese Pharmacopoeia, Japanese Pharmaceutical Excipients, Japan's Specifications and Standards for Food Additives, and the like and ingredients described in Japanese and foreign patent publications and Patent Application Publications (including Japanese Translations of PCT International Applications and Domestic Re-Publications of PCT International Applications) categorized as International Patents Classification IPC of A61K7 and A61K8 can be included in a known combination and in a known formulation ratio or in a known formulation amount.

As publicly and commercially available cosmetics, facial cleansers, body washes, makeup removers, and the like are produced by formulating, for example, a surfactant and a disinfectant as a cleansing component, an oily base material such as polyhydric alcohols and fatty acid esters as an emollient component, a moisturizer, an oily base material, and a thickener as a moisturizing component, and an antiphlogistic as a rough skin-ameliorating component, and by further formulating a preservative, a stabilizer, and the like. A powder can be further added to adjust the viscosity.

Lotions, cosmetic fluids, and the like are produced by formulating, for example, water and an inorganic salt as a base component, an oily base material such as polyhydric alcohols and fatty acid esters and a plant extract as a moisturizing component, a thickener, an antiphlogistic as a rough skin-ameliorating component, and a vitamin, a skin-brightening agent, an antioxidant, an anti-wrinkle agent, an anti-aging agent, a tightening agent, or the like as a functional component.

Creams are produced by formulating, for example, water and a gelator as a base component, an oily base material such as polyhydric alcohols and fatty acid esters as an emollient component, a moisturizer, an oily base material, and a thickener as a moisturizing component, an emulsifier, and an antioxidizing agent or the like as a functional component.

Eye products and the like are produced by formulating, for example, water as a base component, an oily base material such as silicone oils, vegetable oils, and fatty acid esters as an emollient component, a moisturizer such as polyhydric alcohols as a moisturizing component, a thickener, an emulsifier, and an antioxidizing agent or the like as a functional component.

Base makeups, lipstick products, and the like are produced by formulating, for example, water and an inorganic salt as a base component, an oily base material such as silicone oils, fatty acid esters, polyhydric alcohols, and fatty acids as an emollient component, an oily base material such as polyhydric alcohols and a moisturizer as a moisturizing component, and a pigment.

Blushes, powdery foundations, and the like are produced by formulating, for example, a gelator and an inorganic salt as a base component, a thickener as an emollient component, a pigment, an essential oil, and a powder.

Nail color removers and the like are produced by formulating, for example, an oily base material such as esters as a base component, an oily base material such as oils/fats as an emollient component, and a thickener.

UV care performance can be provided to these products by adding a hydrocarbon and a wax as an antioxidizing agent, an inorganic salt and a powder as an ultraviolet-scattering component, an ultraviolet absorber, and the like.

The lipid peptide-based gelator of the present invention, which works as a gelator and/or a thickener in a cosmetic, can replace the gelators and/or the thickeners in these conventional, commercially available cosmetics to increase the safety and the feel in use of these conventional cosmetics.

Examples of the cosmetic that includes the low-molecular lipid peptide-based gelator of the present invention include, but are not limited to, basic care products, makeup products, body products, fragrance products, and hair products.

The basic care products refer to facial cleansers, makeup removers, lotions, milk lotions, cosmetic fluids, facial creams, facial packs, eye products, and other facial skin care products.

Examples thereof include facial cleansers that are bar soaps, foaming cleansers, powder cleansers, and sheet cleansers; makeup removers such as foaming makeup removers, cream-type makeup removers, milk-type makeup removers, lotion-type makeup removers, gel-type makeup removers, oil-type makeup removers, and mask-type makeup removers; lotions such as liposose lotions, moisturizing toners, astringent lotions, cleanser lotions, and multilayered lotions; milk lotions such as emollient lotions, moisturizing lotions, milky lotions, nourishing lotions, nourishing milk lotions, skin moisturizers, moisturizing emulsions, massage lotions, and facial keratin smoothers; cosmetic fluids such as liposome lotions, moisturizing fluids, brightening fluids, and anti-UV fluids; creams such as emollient creams, enriched creams, nourishing creams, vanishing creams, moisturizing creams, night creams, massage creams, cream-type makeup removers, makeup creams, base creams, shaving creams, and facial keratin-softening creams; facial packs such as peel off-type facial packs, powder-type facial packs, wash off-type facial packs, oil-type facial packs, and mask-type makeup removers; eye products such as eye serums, eye gels, and eye creams; UV care products such as facial UV-protection emulsions, sun protection products, sun protectors, UV-care milk lotions, sunscreens, sunscreen creams, and suntan creams; gels such as moisturizing gels, facial peeling products, facial slimming products, and other basic care products.

Examples of the makeup products include base makeup products and point makeup products.

The base makeup products refer to basic makeup that is applied to complement point makeup, and refer to makeup base products, concealers, foundations, and face powder products. Examples thereof include makeup base products such as makeup bases, base creams, color-controlling bases, and UV-screen bases; concealers such as powdery concealers, cream concealers, and liquid concealers; foundations such as powdery foundations, UV-screen foundations, cream foundations, and UV-screen cream foundations; face powder products such as loose powders, pressed powders, face color products, and face powders, and the like.

The point makeup products refer to cosmetics for coloring the skin to make it look beautiful, and examples thereof include eye color products, eyeliners, mascaras, eyebrow products, blushes, lip color products, nail color products, and the like.

Examples thereof include eye color products such as eye color powders, eye color pencils, and eye shadows; eyeliners such as eyeliner pencils and liquid eyeliners; mascaras such as volume-up mascaras, long lash mascaras, curling mascaras, and color mascaras; eyebrow products such as eyebrow pencils, eyebrow powders, and liquid eyebrows; blushes such as powder blushes and cream blushes; lip color products such as lip color products, lipsticks, lipstick products, lip glosses, and lip liners; and nail color products such as nail color products, nail polishes, nail-top coats, base coats, top coats, over-top coats, nail color removers, nail polish removers, nail color thinners, and nail treatments.

Examples of the body products include body lotions, body creams, lip balms, hand creams, UV care products, depilatory products, foot care products, antiperspirants/deodorants, and the like.

Examples thereof include body lotions such as body lotions, body oils, and body mists; body creams such as body creams, body milk lotions, body gels, and body mousses; lip balms such as moisturizing lip balms, UV-care lip balms, and colored lip balms; hand creams such as hand creams and hand gels; UV care products for body such as UV-protection body emulsions, sun protection products, sun protectors, UV-care milk lotions, sunscreens, sunscreen creams, and suntan creams; depilatory products such as depilatory creams, depilatory mousses, depilatory waxes, body hair bleaches, and body shaving creams; foot care products such as foot massage products, foot slimming products, foot peeling products, non-facial exfoliators including exfoliators for heel, and emollient products; antiperspirants/deodorants such as deodorant lotions, deodorant powders, deodorant sprays, and deodorant sticks; and insect repellent products such as insect repellent sprays.

Examples of the fragrance products include perfumes, parfums, eau de parfums, eau de toilettes, eau de colognes, solid perfumes, powder fragrances, perfumed soaps, and bath oils.

Examples of the hair care products include shampoos, hair rinses and conditioners, hair treatments and hair packs, hair styling products, hair sprays and hair glosses, hair growth promoters and pilatories, hair permanent products, and hair coloring products.

Examples thereof include shampoos such as oil shampoos, cream shampoos, conditioning shampoos, anti-dandruff shampoos, shampoos for colored hair, and 2-in-1 shampoos; hair rinses and conditioners such as hair rinses and conditioners, anti-dandruff/scalp-care hair rinses and conditioners, and control hair rinses and conditioners; hair treatments and packs such as damaged hair treatments and packs, damaged hair treatments and packs, anti-dandruff/scalp-care treatments and packs, and control treatments and packs; styling products such as hair foams, hair creams, hair balms, hair gels, hair waters, hair lotions, hair oils, and hair liquids; hair sprays and hair glosses such as hair styling sprays, hair styling mists, and hair glosses, and hair growth promoters and pilatories such as hair growth promoters, pilatories, hair tonics, and hair essences; hair permanent products such as hair relaxers, wave permanent products, permanent pre-treatments, and permanent after-treatments; and hair coloring products such as oxidative hair dyes, hair bleaches, hair coloring pre-treatments, hair coloring after-treatments, and hair manicures.

As in the case of these publicly and commercially available cosmetics, publicly and commercially available external skin preparations include a base component, a gelator, a thickener, and an emulsifier to prepare the dosage form, and include an additional medicinal component such as antiphlogistics. Replacing the gelator and the thickener by the lipid peptide-based gelator of the present invention enhances the safety, the feel in use, the sustained drug efficacy, and the like.

Examples of the external skin preparation that includes the lipid peptide-based gelator of the present invention include, but are not limited to, ointments, patches, liniments, sprays, eye drops, nose drops, ear drops, suppositories, aspiration agents, and the like.

The cosmetic or the external skin preparation of the present invention is in any cosmetic/dosage form, and preferable examples thereof include, but are not limited to, emulsions such as oil-in-water (O/W) emulsions, water-in-oil (W/O) emulsions, W/O/W emulsions, and O/W/O emulsions, oils, solids, liquids, pastes, sticks, volatile oils, powders, jellies, gels, pastes, emulsion polymers, sheets, mists, and sprays. The product of the present invention takes any form, and can be a cosmetic or an external skin preparation as a dispersion, a milk lotion, a cream, a facial pack, a spray, a gel, a sheet, or the like.

The cosmetic, the external skin preparation, and the medical instrument of the present invention include at least one lipid peptide-based gelator that contains a low-molecular lipid peptide or a pharmaceutically usable salt thereof, and at least one macromolecular compound.

The concentration of the lipid peptide-based gelator that is included in the cosmetic or the external skin preparation of the present invention is not particularly limited provided that it is effective, and is 0.0001 to 50% (w/v), preferably 0.0001 to 20% (w/v), more preferably 0.001 to 10% (w/v), and further preferably 0.1 to 5% (w/v), relative to the total volume of the cosmetic or the external skin preparation. When the formulation amount of the lipid peptide-based gelator is 0.0001 to 50% (w/v), the cosmetic or the external skin preparation can feature excellent stretching on the skin surface and the hair surface, excellent permeation into the skin and the hair, no stickiness or crinkles, and retained storage stability.

The cosmetic, the external skin preparation, and the medical instrument of the present invention that include the lipid peptide-based gelator and a macromolecular compound that is exemplified above as the polymers, the thickeners, and the gelators achieve a synergistic effect of the lipid peptide-based gelator and the macromolecular compound. For example, using a macromolecular compound having blood coagulating activity as the macromolecular compound, the effect of the lipid peptide-based gelator to form a fiber that causes physical hemostasis of blood cells and the effect of the macromolecular compound to form a blood clot are obtained. Therefore, the medical instrument of the present invention has an excellent hemostatic effect and can be utilized as a wound dressing base material or a hemostatic agent base material.

The concentration of the macromolecular compound that is included in the cosmetic or the external skin preparation of the present invention is not particularly limited provided that it is effective. For example, in the case of cellulose and a derivative thereof and alginic acid and a salt thereof, the concentration of the macromolecular compound is 0.5 to 3% (w/w) relative to the total mass of the cosmetic or the external skin preparation. When the formulation amount of the macromolecular compound is 0.5 to 3% (w/w), the cosmetic or the external skin preparation of the present invention can effectively exhibit the effect of the macromolecular compound while retaining storage stability.

The concentration of the macromolecular compound that is included in the medical instrument of the present invention is not particularly limited provided that it is effective, and is usually 0.1 to 3% (w/v) relative to the total volume of the medical instrument. When the formulation amount of the macromolecular compound is 0.1 to 3% (w/v), the medical instrument of the present invention can effectively exhibit the effect of the macromolecular compound while retaining storage stability.

Examples of the macromolecular compound may include the macromolecular compounds that are exemplified above as the polymers, the thickeners, and the gelators. Examples of the macromolecular compound having blood coagulating activity include cellulose and derivatives thereof, alginic acid and salts thereof, gum arabic, and the like, and among these, sodium alginate and gum arabic are preferable from the viewpoint of the hemostatic effect.

The cosmetic, the external skin preparation, and the medical instrument of the present invention that include the lipid peptide-based gelator and, instead of the macromolecular compound, a protein also achieve a synergistic effect of the lipid peptide-based gelator and the protein.

Examples of the protein are the same ones as those mentioned above as the polymers, the thickeners, and the gelators.

EXAMPLES

The present invention will be described in detail by Examples and Test Examples. The present invention is, however, not limited to these Examples and Test Examples.

Abbreviations to be used in the following examples mean as follows.
Gly: glycine
His: histidine
DMF: dimethylformamide
TFA: trifluoroacetic acid (Watanabe Chemical Industries, LTD.)
DMSO: dimethylsulfoxide
WSCD: 1-ethyl-3-(3-dimethylaminopropyl)carbodiimide
[Synthesis of Lipid Peptide]
A lipid peptide was synthesized by the method shown below.

Synthesis Example 1

Method for Protecting-Group-Free Synthesis of N-Palmitoyl-Gly-His TFA Salt

<Synthesis of N-Palmitoyloxy-Succinimide>
To a solution of 165 mL (0.544 mol) of palmitoyl chloride in 1 L of chloroform while cooled with ice with stirring, 69.8 g (0.598 mol) of N-hydroxysuccinimide was gradually added, and 83.1 mL (0.598 mol) of triethylamine was added dropwise thereto over 30 minutes. The resultant solution was stirred for 30 minutes while cooled with ice and for another 7 hours during which the resultant solution gradually reached room temperature. After washed with 500 mL of water three times, the resultant solution was dried over magnesium sulfate and was then concentrated under reduced pressure to obtain 260.3 g (quant) of a colorless solid.

$^1$H-NMR (300 MHz DMSO-$d_6$ δppm): 2.80 (4H, s), 2.65 (2H, t, J=7.2 Hz), 1.61 (2H, quintet, J=7.2 Hz), 1.24 (24H, s), 0.85 (3H, t, J=6.3 Hz).

<Synthesis of N-Palmitoyl-Gly>
260.3 g of the N-palmitoyloxy-succinimide synthesized above as a whole was suspended in 750 ml of DMF and, to the resultant solution while cooled with ice with stirring, 56.3 g (0.750 mol) of Gly and 83.2 mL (0.598 mol) of triethylamine dissolved in 250 ml of water were added dropwise. The resultant solution was stirred for another 30 minutes while cooled with ice and for another 15 hours during which the resultant solution gradually reached room temperature. To an aqueous solution obtained by dissolving 100 mL of 6 N hydrochloric acid in 1 L of water and adjusting the pH to pH 3, while cooled with ice with stirring, the reaction solution was added dropwise to precipitate a solid, which was filtered off. The resultant product was washed with 2 L of water and then with 1 L of hexane, and was then collected to obtain 114 g (67%) of a desired compound.

$^1$H-NMR (300 MHz DMSO-$d_6$ δppm): 8.10 (1H, t, J=6 Hz), 3.71 (2H, d, J=6 Hz), 2.10 (2H, t, J=7.2 Hz), 1.48 (2H, m), 1.23 (24H, s), 0.85 (3H, t, J=6.3 Hz).

<Synthesis of N-Palmitoyloxy-Glycyloxysuccinimide>
114 g (0.364 mol) of the N-palmitoyl-Gly synthesized above and 44.0 g (0.382 mol) of N-hydroxysuccinimide were suspended in 620 mL of DMF and, to the resultant solution while cooled with ice with stirring, 73.2 g (0.382 mol) of WSCD hydrochloride was added. The resultant solution was stirred for 30 minutes while cooled with ice and then for another 20 hours at room temperature. 1.5 L of ice water was added thereto, and insoluble matter was filtered off. The resulting insoluble matter was washed with 5 L of water and then with 1.5 L of ether, and the resultant product was dried under reduced pressure to quantitatively obtain 198 g of a colorless solid.

<Synthesis of N-Palmitoyl-Gly-His TFA Salt>

198 g of the N-palmitoyloxy-glycyloxysuccinimide synthesized above as a whole was suspended in DMF and, to the resultant solution while cooled with ice with stirring, a suspension of 113 g (0.728 mol) of L-histidine, 55.6 mL (0.400 mol) of triethylamine, and 350 ml of water was added. Subsequently, the resultant solution was stirred for 30 minutes while cooled with ice, and the temperature was then raised to room temperature, followed by stirring for another 17 hours. The precipitated solid was filtered off as it was to obtain a solid. The resultant product was added to a mixed solution of 120 mL of trifluoroacetic acid and 1.5 L of ice water, followed by stirring and then filtering insoluble matter. The resulting solid was placed in a jug to be washed with 2 L of water three times, and was subsequently dried under reduced pressure. The resulting dry solid was dissolved in 400 mL of trifluoroacetic acid, and a small amount of insoluble matter was filtered off with a membrane filter. The filtrate was concentrated under reduced pressure to about half the amount, which was then washed with diethyl ether. The solid was dried under reduced pressure and was washed with water an appropriate number of times, and the resulting solid was dried under reduced pressure to obtain 112 g (54%) of a colorless solid.

Synthesis Example 2

Synthesis of N-Palmitoyl-Gly-His (Free Form)

14.2 g (91.6 mmol) of histidine, 30.0 g (91.6 mmol) of N-palmitoyl-Gly-methyl, and 300 g of toluene were added to a 500-mL four-necked flask, to which 35.3 g (183.2 mmol) of a 28% methanol solution of sodium methoxide as a base was added, and the resultant solution was heated in an oil bath to 60° C. and was stirred for 1 hour. Subsequently, the resulting solution from which the oil bath was removed was left to cool to reach 25° C., was reprecipitated with 600 g of acetone, and was filtered off. The resulting solid was dissolved in a mixed solution of 600 g of water and 750 g of methanol, to which 30.5 mL (183.2 mmol) of 6 N hydrochloric acid was added for neutralization to precipitate a solid, which was filtered off. The resulting solid was then dissolved in a mixed solution of 120 g of tetrahydrofuran and 30 g of water at 60° C., to which 150 g of ethyl acetate was added, and the resultant solution was cooled from 60° C. to 30° C. Subsequently, the precipitated solid was filtrated. The resulting solid was heated in a solvent of 120 g of tetrahydrofuran and 60 g of acetonitrile to 60° C., was stirred for 1 hour, and then cooled, followed by filtration. The resulting solid was washed with 120 g of water and filtrated, followed by drying under reduced pressure to obtain 26.9 g (yield: 65%) of a white crystal of a free form of N-palmitoyl-Gly-His.

[Preparation of 70% Glycerin-Water]

Ultrapure water (manufactured by Kurita Water Industries Ltd.) was added to 3.0 g of glycerin (manufactured by JUNSEI CHEMICAL CO., LTD.) to achieve a concentration of 70% (w/v), and thus 70% glycerin-water was prepared. A product that was stable at room temperature for 2 months or longer was used for testing.

[Evaluation of Feel in Use]

A cosmetic or an external skin preparation was prepared according to Examples 1 to 9 or Comparative Examples 1 to 3, and stretching on the skin surface, permeation into the skin, stickiness, and crinkles were evaluated based on the following evaluation criterions. Evaluation results are listed in Table 12.

[Evaluation of Stickiness]

A cosmetic or an external skin preparation was prepared according to Examples 10 to 13 or Comparative Example 4 or 5, and stretching on the skin surface, permeation into the skin, and stickiness were evaluated based on the following evaluation criterions. Evaluation results are listed in Table 13.

<Method for Testing Feel in Use of Solid and Spray>

A sample was applied on the back of the left hand with a spatula in a test of a solid, or in a test of a spray, a sample was sprayed once at the back of the left hand. The applied or sprayed sample was rubbed on the skin for a distance of 10 to 20 cm back and forth 50 to 100 times, and the feel in use during the rubbing was evaluated. Crinkles were evaluated when the sample dried.

<Evaluation Criterion for Stretching on Skin Surface>

When a cosmetic or an external skin preparation was applied on the skin, a sample that stretched on the skin surface smoothly without roughness was evaluated as ○, while a sample that stretched smoothly or with roughness was evaluated as X.

<Evaluation Criterion for Permeation into Skin>

When a cosmetic or an external skin preparation was applied on the skin, a sample that rapidly permeated the skin and was absorbed into the skin to moisturize it was evaluated as ○, while a sample that was not absorbed into the skin to moisturize it was evaluated as X.

<Evaluation Criterion for Stickiness>

After a cosmetic or an external skin preparation was applied on the skin, a sample that caused no stickiness lingering on the skin surface was evaluated as ○, while a sample that caused stickiness lingering on the skin surface was evaluated as X.

<Evaluation Criterion for Crinkles>

After a cosmetic or an external skin preparation was applied on the skin and dried, a sample that caused no crinkles was evaluated as ○, a sample that caused little or minimal crinkles was evaluated as Δ, and a sample that caused crinkles was evaluated as X.

Example 1

Feel in Use of Palmitoyl-Gly-His TFA Salt-Formulated, Gel-Form Cosmetic

The palmitoyl-Gly-His TFA salt synthesized in Synthesis Example 1, polyethylene glycol 400 (manufactured by Wako Pure Chemical Industries, Ltd.), phenoxyethanol (manufactured by JUNSEI CHEMICAL CO., LTD.), 1,3-butanediol (manufactured by KANTO CHEMICAL CO., INC.), glycerin (manufactured by JUNSEI CHEMICAL CO., LTD.), ethanol (manufactured by KANTO CHEMICAL CO., INC.), and deionized water (Japanese Pharmacopoeia-grade sterilized water manufactured by KYOEI Pharmaceutical Industries, Ltd.) in the formulation amounts listed in Table 1 were added to a screw tube (manufactured by Maruemu Corporation, No. 7), which was heated in a dry bath incubator (manufactured by First Gene) (between 90° C. and 105° C., 10 minutes) and was left still standing at room temperature for gelation. A product that was stable at room temperature for 6 months or longer was used for testing. Evaluation of the feel in use is listed in Table 12.

TABLE 1

Palmitoyl-Gly-His TFA salt-formulated, gel-form cosmetic

| | Formulation amount |
|---|---|
| Palmitoyl-Gly-His TFA salt | 49.5 mg |
| Deionized water | 1 mL |
| Phenoxyethanol | 0.25 mL |
| Ethanol | 1.25 mL |
| 1,3-Butanediol | 0.25 mL |
| PEG 400 | 1 mL |
| Glycerin | 6.25 mL |

Example 2

Feel in Use of Palmitoyl-Gly-His TFA Salt-Formulated, Gel-Form External Skin Preparation that is Formulated with Indomethacin and 1-Menthol The palmitoyl-Gly-His TFA salt synthesized in Synthesis Example 1, indomethacin (manufactured by TOKYO CHEMICAL INDUSTRY CO., LTD.), 1-menthol (manufactured by JUNSEI CHEMICAL CO., LTD.), polyethylene glycol 400 (manufactured by Wako Pure Chemical Industries, Ltd.), phenoxyethanol (manufactured by JUNSEI CHEMICAL CO., LTD.), 1,3-butanediol (manufactured by KANTO CHEMICAL CO., INC.), glycerin (manufactured by JUNSEI CHEMICAL CO., LTD.), ethanol (manufactured by KANTO CHEMICAL CO., INC.), and deionized water (Japanese Pharmacopoeia-grade sterilized water manufactured by KYOEI Pharmaceutical Industries, Ltd.) in the formulation amounts listed in Table 2 were added to a screw tube (manufactured by Maruemu Corporation, No. 7), which was heated in a dry bath incubator (manufactured by First Gene) (between 90° C. and 105° C., 10 minutes) and was left still standing at room temperature for gelation. A product that was stable at room temperature for 6 months or longer was used for testing. Evaluation of the feel in use is listed in Table 12.

TABLE 2

Palmitoyl-Gly-His TFA salt-formulated, gel-form external skin preparation that is formulated with indomethacin and 1-menthol

| | Formulation amount |
|---|---|
| Palmitoyl-Gly-His TFA salt | 49.1 mg |
| Deionized water | 1 mL |
| Indomethacin | 99.3 mg |
| L-menthol | 300 mg |
| Phenoxyethanol | 0.05 mL |
| Ethanol | 1.25 mL |
| 1,3-Butanediol | 0.7 mL |
| PEG 400 | 2.5 mL |
| Glycerin | 0.45 mL |

Example 3

Feel in Use of Palmitoyl-Gly-His TFA Salt-Formulated, Cream-Form External Skin Preparation that is Formulated with Indomethacin The palmitoyl-Gly-His TFA salt synthesized in Synthesis Example 1, indomethacin (manufactured by TOKYO CHEMICAL INDUSTRY CO., LTD.), ethanol (manufactured by KANTO CHEMICAL CO., INC.), and deionized water (Japanese Pharmacopoeia-grade sterilized water manufactured by KYOEI Pharmaceutical Industries, Ltd.) in the formulation amounts listed in Table 1 were added to a screw tube (manufactured by Maruemu Corporation, No. 7), which was heated in a dry bath incubator (manufactured by First Gene) (between 90° C. and 105° C., 10 minutes) and was left still standing at room temperature to solidify the resultant into cream. A product that was stable at room temperature for 6 months or longer was used for testing. Evaluation of the feel in use is listed in Table 12.

TABLE 3

Palmitoyl-Gly-His TFA salt-formulated, cream-form external skin preparation that is formulated with indomethacin

| | Formulation amount |
|---|---|
| Palmitoyl-Gly-His TFA salt | 49.7 mg |
| Deionized water | 6.3 mL |
| Indomethacin | 113.2 mg |
| Ethanol | 1 mL |
| Glycerin | 2.7 mL |

Example 4

Feel in Use of Glycerin-Containing, Gel-Form Cosmetic that Includes a Free Form of Palmitoyl-Gly-His The free form of palmitoyl-Gly-His synthesized in Synthesis Example 2, glycerin (manufactured by JUNSEI CHEMICAL CO., LTD.), 2-propanol (KANTO CHEMICAL CO., INC.), lactic acid (manufactured by JUNSEI CHEMICAL CO., LTD.), potassium lactate (manufactured by KANTO CHEMICAL CO., INC.), and deionized water (ultrapure water manufactured by Kurita Water Industries Ltd.) in the formulation amounts listed in Table 4 were added to a screw tube (Maruemu Corporation, No. 7), which was heated in a dry bath incubator (manufactured by First Gene) (80° C., 15 minutes) and was left still standing at room temperature for gelation. A product that was stable at room temperature for 1 month or longer was used for testing. Evaluation of the feel in use is listed in Table 12.

TABLE 4

Glycerin-containing, gel-form cosmetic that includes free form of palmitoyl-Gly-His

| | Formulation amount |
|---|---|
| Free form of palmitoyl-Gly-His | 0.02 g |
| Glycerin | 5.55 g |
| Lactic acid | 0.0125 g |
| Potassium lactate | 0.4875 g |
| 2-Propanol | 1 g |
| Deionized water | 3 g |

Example 5

Feel in Use of Propylene Glycol-Containing, Gel-Form Cosmetic that Includes Free Form of Palmitoyl-Gly-His The free form of palmitoyl-Gly-His synthesized in Synthesis Example 2, propylene glycol (manufactured by JUNSEI CHEMICAL CO., LTD.), lactic acid (manufactured by JUNSEI CHEMICAL CO., LTD.), potassium lactate (manufactured by KANTO CHEMICAL CO., INC.), and deionized water (ultrapure water manufactured by Kurita Water Industries Ltd.) in the formulation amounts listed in Table 5 were added to a screw tube (manufactured by Maruemu Corporation, No. 7), which was heated in a dry bath incubator (manufactured by First Gene) (80° C., 15 minutes) and was left still standing at room temperature for gelation. A product that was stable at room temperature for 1 month or longer was used for testing. Evaluation of the feel in use is listed in Table 12.

TABLE 5

Propylene glycol-containing, gel-form cosmetic that includes free form of palmitoyl-Gly-His

| | Formulation amount |
|---|---|
| Free form of palmitoyl-Gly-His | 0.025 g |
| Propylene glycol | 6.5 g |
| Lactic acid | 0.025 g |
| Potassium lactate | 0.475 g |
| Deionized water | 3 g |

Example 6

Feel in Use of 1,3-Butanediol-Containing, Gel-Form 1 Cosmetic that Includes Free Form of Palmitoyl-Gly-His The free form of palmitoyl-Gly-His synthesized in Synthesis Example 2, 1,3-butanediol (manufactured by KANTO CHEMICAL CO., INC.), lactic acid (manufactured by JUNSEI CHEMICAL CO., LTD.), potassium lactate (manufactured by KANTO CHEMICAL CO., INC.), and deionized water (ultrapure water manufactured by Kurita Water Industries Ltd.) in the formulation amounts listed in Table 6 were added to a screw tube (manufactured by Maruemu Corporation, No. 7), which was heated in a dry bath incubator (manufactured by First Gene) (80° C., 15 minutes) and was left still standing at room temperature for gelation. A product that was stable at room temperature for 1 month or longer was used for testing. Evaluation of the feel in use is listed in Table 12.

TABLE 6

1,3-Butanediol-containing, gel-form cosmetic that includes free form of palmitoyl-Gly-His

| | Formulation amount |
|---|---|
| Free form of palmitoyl-Gly-His | 0.025 g |
| 1,3-Butanediol | 6.5 g |
| Lactic acid | 0.0125 g |
| Potassium lactate | 0.4875 g |
| Deionized water | 3 g |

Example 7

Feel in Use of 70% Glycerin-Water-Containing, Sprayable Gel-Form Cosmetic that Includes Free Form of Palmitoyl-Gly-His 0.010 g of the free form of palmitoyl-Gly-His synthesized in Synthesis Example 2 was placed in a screw tube (manufactured by Maruemu Corporation, No. 5), and 10 mL of 70% glycerin-water was added thereto. The resultant solution was heated in a dry bath incubator (manufactured by First Gene) (98° C., 30 minutes), and a 6-mL aliquot of the resulting solution was transferred to a spray vial (manufactured by Maruemu Corporation, No. 3L), which was left to cool to reach room temperature for gelation.

A state in which, after cooling down, the solution lost fluidity and did not flow down when the spray vial was inverted was confirmed, and thus it was determined that the solution had been gelled. Evaluation of the feel in use is listed in Table 12.

Example 8

Feel in Use of 70% Glycerin-Water-Containing, Sprayable Gel-Form Cosmetic that Includes Free Form of Palmitoyl-Gly-His at 0.2%

0.025 g of the free form of palmitoyl-Gly-His synthesized in Synthesis Example 2 was placed in a screw tube (manufactured by Maruemu Corporation, No. 5), and 12.5 mL of 70% glycerin-water was added thereto. The resultant solution was heated in a dry bath incubator (manufactured by First Gene) (98° C., 30 minutes), and a 6-mL aliquot of the resulting solution was transferred to a spray vial (manufactured by Maruemu Corporation, No. 3L), which was left to cool to reach room temperature for gelation.

A state in which, after cooling down, the solution lost fluidity and did not flow down when the spray vial was inverted was confirmed, and thus it was determined that the solution had been gelled. Evaluation of the feel in use is listed in Table 12.

Example 9

Feel in Use of 70% Glycerin-Water-Containing, Sprayable Sol (Water Dispersion)-Form Cosmetic that Includes Free Form of Palmitoyl-Gly-His at 0.2%

0.025 g of the free form of palmitoyl-Gly-His synthesized in Synthesis Example 2 was placed in a screw tube (manufactured by Maruemu Corporation, No. 5), and 12.5 mL of 70% glycerin-water was added thereto. The resultant solution was heated in a dry bath incubator (manufactured by First Gene) (98° C., 30 minutes), and a 6-mL aliquot of the resulting solution was transferred to a spray vial (manufactured by Maruemu Corporation, No. 3L), which was left to cool to reach room temperature.

A state in which, after cooling down, the solution lost fluidity and did not flow down when the spray vial was inverted was confirmed, and thus it was determined that the solution had been gelled. The resulting gel was vibrated for 10 minutes in a microtube mixer (manufactured by Nissin Scientific Corporation) at 2,600 rpm to mechanically disintegrate the gel, and thus a sol (water dispersion) was obtained. Evaluation of the feel in use is listed in Table 12.

TABLE 7

70% Glycerin-water-containing, sprayable gel- or sprayable sol (sprayable water dispersion)-form cosmetic that includes free form of palmitoyl-Gly-His at 0.1% or 0.2%

|  | Example 7 | Example 8 | Example 9 |
|---|---|---|---|
| Free form of palmitoyl-Gly-His | 0.010 g | 0.025 g | 0.025 g |
| 70% Glycerin-water | 10 mL | 12.5 mL | 12.5 mL |
| Form | Gel | Gel | Sol |

Example 10

Stickiness of 70% Glycerin-Water-Containing, Gel-Form External Skin Preparation that Includes Free Form of Palmitoyl-Gly-His and is Formulated with Indomethacin and Camphor The free form of palmitoyl-Gly-His synthesized in Synthesis Example 2, indomethacin (manufactured by TOKYO CHEMICAL INDUSTRY CO., LTD.), camphor (manufactured by JUNSEI CHEMICAL CO., LTD.), glycerin (manufactured by JUNSEI CHEMICAL CO., LTD.), and ultrapure water (manufactured by Kurita Water Industries Ltd.) in the formulation amounts listed in Table 8 were added to a screw tube (manufactured by Maruemu Corporation, No. 5), which was heated in a dry bath incubator (manufactured by First Gene) (100° C., 30 minutes) and was left still standing at room temperature for gelation. A product that was stable at room temperature for 1 month or longer was used for testing. Evaluation of the stickiness is listed in Table 13.

TABLE 8

70% glycerin-water-containing, gel-form external skin preparation that includes free form of palmitoyl-Gly-His and is formulated with indomethacin and camphor

|  | Formulation amount |
|---|---|
| Free form of palmitoyl-Gly-His | 0.015 g |
| 70% Glycerin-water | 6 mL |
| Indomethacin | 0.010 g |
| Camphor | 0.010 g |

Example 11

Stickiness of 70% Glycerin-Water-Containing, Gel-Form External Skin Preparation that Includes Free Form of Palmitoyl-Gly-His and is Formulated with Indomethacin and Benzalkonium The free form of palmitoyl-Gly-His synthesized in Synthesis Example 2, indomethacin (manufactured by TOKYO CHEMICAL INDUSTRY CO., LTD.), benzalkonium (50% benzalkonium chloride solution manufactured by JUNSEI CHEMICAL CO., LTD.), glycerin (manufactured by JUNSEI CHEMICAL CO., LTD.), and ultrapure water (manufactured by Kurita Water Industries Ltd.) in the formulation amounts listed in Table 9 were added to a screw tube (manufactured by Maruemu Corporation, No. 5), which was heated in a dry bath incubator (manufactured by First Gene) (100° C., 30 minutes) and was left still standing at room temperature for gelation. A product that was stable at room temperature for 6 months or longer was used for testing. Evaluation of the stickiness is listed in Table 13.

TABLE 9

70% glycerin-water-containing, gel-form external skin preparation that includes free form of palmitoyl-Gly-His and is formulated with indomethacin and benzalkonium

|  | Formulation amount |
|---|---|
| Free form of palmitoyl-Gly-His | 0.015 g |
| 70% Glycerin-water | 6 mL |
| Indomethacin | 0.010 g |
| 50% Benzalkonium | 0.1 mL |

Example 12

Stickiness of 70% Glycerin-Water-Containing, Gel-Form Cosmetic that Includes Free Form of Palmitoyl-Gly-His and is Formulated with Ascorbyl 2-Glucoside The free form of palmitoyl-Gly-His synthesized in Synthesis Example 2, indomethacin (manufactured by TOKYO CHEMICAL INDUSTRY CO., LTD.), ascorbyl 2-glucoside (manufactured by Wako Pure Chemical Industries, Ltd.), glycerin (manufactured by JUNSEI CHEMICAL CO., LTD.), and ultrapure water (manufactured by Kurita Water Industries Ltd.) in the formulation amounts listed in Table 10 were added to a screw tube (manufactured by Maruemu Corporation, No. 5), which was heated in a dry bath incubator (manufactured by First Gene) (80° C., 30 minutes) and was left still standing at room temperature for gelation. A product that was stable at room temperature for 1 month or longer was used for testing. Evaluation of the stickiness is listed in Table 13.

TABLE 10

70% glycerin-water-containing, gel-form cosmetic that includes free form of palmitoyl-Gly-His and is formulated with ascorbyl 2-glucoside

|  | Formulation amount |
|---|---|
| Free form of palmitoyl-Gly-His | 0.0153 g |
| 70% Glycerin-water | 6.12 mL |
| Ascorbyl 2-glucoside | 0.110 g |

Example 13

Stickiness of 70% Glycerin-Water-Containing, Gel-Form External Skin Preparation that Includes Free Form of Palmitoyl-Gly-His and is Formulated with Ascorbyl 2-Glucoside and Indomethacin The free form of palmitoyl-Gly-His synthesized in Synthesis Example 2, indomethacin (manufactured by TOKYO CHEMICAL INDUSTRY CO., LTD.), ascorbyl 2-glucoside (manufactured by Wako Pure Chemical Industries, Ltd.), glycerin (manufactured by JUNSEI CHEMICAL CO., LTD.), and ultrapure water (manufactured by Kurita Water Industries Ltd.) in the formulation amounts listed in Table 11 were added to a screw tube (manufactured by Maruemu Corporation, No. 5), which was heated in a dry bath incubator (manufactured by First Gene) (80° C., 30 minutes) and was left still standing at room temperature for gelation. A product that was stable at room temperature for 1 month or longer was used for testing. Evaluation of the stickiness is listed in Table 13.

TABLE 11

70% glycerin-water-containing, gel-form external skin preparation that includes free form of palmitoyl-Gly-His and is formulated with ascorbyl 2-glucoside and indomethacin

| | Formulation amount |
|---|---|
| Free form of palmitoyl-Gly-His | 0.0101 g |
| 70% Glycerin-water | 4.04 mL |
| Indomethacin | 0.010 mg |
| Ascorbyl 2-glucoside | 0.110 g |

An aqueous glycerin solution-based cosmetic that is formulated with a carboxyvinyl polymer, gellan gum, or carboxymethylcellulose was prepared, and the feel in use thereof was tested. Evaluation of the feel in use is listed in Table 12.

Comparative Example 1

Feel in Use of Aqueous Glycerin Solution-Based Cosmetic that is Formulated with 0.15% Carboxyvinyl Polymer To 0.252 g of Carbopol 940 (manufactured by ITO, Inc.), which is a carboxyvinyl polymer, Japanese Pharmacopoeia-grade sterilized water (manufactured by KYOEI Pharmaceutical Industries, Ltd.) was added to achieve a concentration of 2% (w/v), followed by warming the resultant solution in a water bath until it dissolved. 15 µL of 6 N NaOH was added thereto, and the resultant solution was left still standing at room temperature to be solidified. A product that was stable at room temperature for 6 months or longer was used for testing. Evaluation of the feel in use is listed in Table 13.

Comparative Example 2

Feel in Use of Aqueous Glycerin Solution-Based Cosmetic that is Formulated with 2% Gellan Gum To 0.504 g of gellan gum (manufactured by KANTO CHEMICAL CO., INC.), Japanese Pharmacopoeia-grade sterilized water (manufactured by KYOEI Pharmaceutical Industries, Ltd.) was added to achieve a concentration of 2% (w/v), followed by warming the resultant solution in a water bath until it dissolved. The resultant solution was left still standing at room temperature to be solidified. A product that was stable at room temperature for 6 months or longer was used for testing. Evaluation of the feel in use is listed in Table 12.

Comparative Example 3

Feel in Use of Aqueous Glycerin Solution-Based Cosmetic that is Formulated with 5% Carboxymethylcellulose To 0.5 g of carboxymethylcellulose (manufactured by As One Corporation), Japanese Pharmacopoeia-grade sterilized water (manufactured by KYOEI Pharmaceutical Industries, Ltd.) was added to achieve a concentration of 5% (w/v), followed by warming the resultant solution in a water bath until it dissolved. The resultant solution was left still standing at room temperature to be solidified. A product that was stable at room temperature for 6 months or longer was used for testing. Evaluation of the feel in use is listed in Table 12.

Comparative Example 4

Stickiness of 70% Glycerin-Water

The 70% glycerin-water prepared above was used for testing. Evaluation of the stickiness is listed in Table 13.

Comparative Example 5

Stickiness of 14% Glycerin-Water 8 mL of ultrapure water (manufactured by Kurita Water Industries Ltd.) was added to 2 mL of 70% glycerin-water to obtain 14% glycerin. A product that was stable at room temperature for 2 months or longer was used for testing. Evaluation of the stickiness is listed in Table 13.

TABLE 12

Evaluation results of feel in use in Examples 1 to 9 and Comparative Examples 1 to 3

| | Example | | | | | | | | | Comparative Example | | |
|---|---|---|---|---|---|---|---|---|---|---|---|---|
| | 1 | 2 | 3 | 4 | 5 | 6 | 7 | 8 | 9 | 1 | 2 | 3 |
| Stretching on skin surface | ○ | ○ | ○ | ○ | ○ | ○ | ○ | ○ | ○ | ○ | ○ | ○ |
| Permeation into skin | ○ | ○ | ○ | ○ | ○ | ○ | ○ | ○ | ○ | ○ | ○ | ○ |
| Stickiness | ○ | ○ | ○ | ○ | ○ | ○ | ○ | ○ | ○ | X | X | X |
| Crinkles | ○ | ○ | ○ | ○ | ○ | ○ | ○ | ○ | ○ | X | X | X |

TABLE 13

Evaluation results of stickiness in Examples 10 to 13 and Comparative Examples 4 and 5

| | Example | | | | Comparative Example | |
|---|---|---|---|---|---|---|
| | 10 | 11 | 12 | 13 | 4 | 5 |
| Stretching on skin surface | ○ | ○ | ○ | ○ | ○ | ○ |
| Permeation into skin | ○ | ○ | ○ | ○ | ○ | ○ |
| Stickiness | ○ | ○ | ○ | ○ | X | X |

According to the results of Examples 1 to 9 in Table 12, cosmetics that include the lipid peptide-based gelator of the present invention; water, a (polyhydric) alcohol, or a mixed solution of water and a (polyhydric) alcohol; and either of benzalkonium or a functional material such as ascorbyl 2-glucoside; and external skin preparations that include indomethacin, 1-menthol, camphor, and the like had an excellent feel in use, e.g., excellent stretching on the skin surface, excellent permeation into the skin, no lingering stickiness, and no crinkles. In contrast, in Comparative Examples 1 to 3 in each of which a conventional gelator such as polysaccharide thickeners and polymers was used, each product was excellent in stretching on the skin surface and permeation into the skin and, however, had inferior feel in use that caused lingering stickiness and crinkles.

According to the results of Examples 10 to 13 in Table 13, the cosmetic and the external skin preparation that include the lipid peptide-based gelator of the present invention caused no stickiness, while conventional glycerin-water caused stickiness as shown in Comparative Example 4 or 5.

Therefore, the cosmetic and the external skin preparation that include the lipid peptide-based gelator of the present invention gave excellent results.

In these evaluation tests, no skin problems such as skin irritation and itching, or the like were observed.

A cosmetic that is formulated with a macromolecular compound was prepared according to Examples 14 to 19 and was evaluated based on [Evaluation of feel in use] above. Evaluation results are listed in Table 20.

[Preparation of Glycerin Dispersion Containing a Free Form of Palmitoyl-Gly-His at 5%]

125 g of glycerin (manufactured by Wako Pure Chemical Industries, Ltd.) and a stirrer were placed in a round-bottom flask (200 mL), which was heated in an oil bath to 105° C., followed by stirring. Thereto, 6.25 g of the free form of palmitoyl-Gly-His that was synthesized in Synthesis Example 2 and was pulverized in a ball mill (ULTRA-TURRAX [registered trademark] Tube Drive manufactured by IRA) was added, and the resultant was heated for 30 minutes to obtain a translucent solution. Subsequently, the resulting solution was cooled at room temperature and was lightly mixed with a spatula to obtain a white viscous dispersion.

[Preparation of Propylene Glycol Dispersion Containing a Free Form of Palmitoyl-Gly-His at 1.5%]

0.4 g of the free form of palmitoyl-Gly-His synthesized in Synthesis Example 2 and propylene glycol (manufactured by JUNSEI CHEMICAL CO., LTD.) were added to a lidded glass vial tube (manufactured by Maruemu Corporation, No. 5) to achieve a total weight of 26.7 g. The resultant solution was heated in a dry bath incubator (manufactured by First Gene) (90° C., 30 minutes) and was cooled at room temperature to obtain a dispersion.

[Preparation of Propylene Glycol Dispersion Containing a Free Form of Palmitoyl-Gly-His at 1%]

1 g of the free form of palmitoyl-Gly-His synthesized in Synthesis Example 2 and propylene glycol (manufactured by JUNSEI CHEMICAL CO., LTD.) were added to a lidded glass vial tube (manufactured by Maruemu Corporation, No. 5) to achieve a total weight of 100 g. The resultant solution was heated in a dry bath incubator (manufactured by First Gene) (90° C., 60 minutes) and was cooled at room temperature to obtain a dispersion.

[Preparation of 2% Aqueous Cellulose Solution]

25 mL of deionized water was added to a lidded glass vial tube (manufactured by Maruemu Corporation, No. 7), which was heated in a dry bath incubator (manufactured by First Gene) (100° C., 10 minutes). Subsequently, 0.5 g of hydroxymethylpropyl cellulose (SE-06-HPMC manufactured by Shin-Etsu Chemical Co., Ltd.) was added, and the resultant solution was heated for another 20 minutes while, as needed, lightly shaken, followed by cooling at room temperature to obtain an aqueous solution.

[Preparation of 1% Aqueous Propylene Glycol Alginate Solution]

0.5 g of propylene glycol alginate (manufactured by JUNSEI CHEMICAL CO., LTD.) and deionized water were added to a lidded glass vial tube (manufactured by Maruemu Corporation, No. 7) to achieve a total volume of 50 mL. The resultant solution was lightly shaken to obtain an aqueous solution.

[Preparation of 1% Aqueous Sodium Alginate Solution]

0.5 g of sodium alginate (manufactured by JUNSEI CHEMICAL CO., LTD.) and deionized water were added to a lidded glass vial tube (manufactured by Maruemu Corporation, No. 7) to achieve a total volume of 50 mL. The resultant solution was lightly shaken to obtain an aqueous solution.

[Preparation of 5% Aqueous Polyvinyl Alcohol Solution]

25 mL of deionized water was added to a lidded glass vial tube (manufactured by Maruemu Corporation, No. 7), which was heated in a dry bath incubator (manufactured by First Gene) (100° C., 10 minutes). Subsequently, 1.25 g of Poval 117 (manufactured by KURARAY CO., LTD.) was added, and the resultant solution was heated for another 60 minutes while, as needed, lightly shaken. Dissolution of the resultant solution was confirmed by visual observation, and the resultant solution was cooled at room temperature to obtain an aqueous solution.

[Preparation of 0.5% Aqueous Methylcellulose Solution]

25 mL of deionized water was added to a lidded glass vial tube (manufactured by Maruemu Corporation, No. 7), which was heated in a dry bath incubator (manufactured by First Gene) (100° C., 10 minutes). Subsequently, 0.125 g of methylcellulose (manufactured by Sigma-Aldrich) was added, and the resultant solution was heated for another 90 minutes while, as needed, lightly shaken, followed by cooling at room temperature to obtain an aqueous solution.

Example 14

Feel in Use of Sprayable Gel-Form Cosmetic that Includes a Free Form of Palmitoyl-Gly-His and is Formulated with Cellulose 1 g of a glycerin dispersion containing a free form of palmitoyl-Gly-His at 5% was placed in a screw tube (manufactured by Maruemu Corporation, No. 5), and 4.5 g of a 2% aqueous cellulose solution and 4.5 g of deionized water were added thereto. The resultant solution was heated in a dry bath incubator (manufactured by First Gene) (90° C., 20 minutes), and the resulting solution was transferred to a spray vial (manufactured by Maruemu Corporation, No. 3L), which was left to cool to reach room temperature, A state in which, after cooling down, the solution lost fluidity and did not flow down when the spray vial was inverted was confirmed, and thus it was determined that the solution had been gelled. Evaluation of the feel in use is listed in Table 24.

TABLE 14

| Sprayable gel-form cosmetic that includes free form of palmitoyl-Gly-His and is formulated with cellulose | |
|---|---|
| | Formulation amount |
| Glycerin dispersion containing free form of palmitoyl-Gly-His at 5% | 1 g |
| 2% Aqueous cellulose solution | 4.5 g |
| Deionized water | 4.5 g |

Example 15

Feel in Use of Sprayable Gel-Form Cosmetic that Includes Free Form of Palmitoyl-Gly-His and is Formulated with Propylene Glycol Alginate 1 g of a glycerin dispersion containing a free form of palmitoyl-Gly-His at 5% was placed in a screw tube (manufactured by Maruemu Corporation, No. 5), and 9 g of a 1% aqueous propylene glycol alginate solution was added thereto. The resultant solution was heated in a dry bath incubator (manufactured by First Gene) (80° C., 20 minutes), and the resulting solution was transferred to a spray vial (manufactured by Maruemu Corporation, No. 3L), which was left to cool to reach room temperature.

A state in which, after cooling down, the solution lost fluidity and did not flow down when the spray vial was inverted was confirmed, and thus it was determined that the solution had been gelled. Evaluation of the feel in use is listed in Table 24.

TABLE 15

Sprayable gel-form cosmetic that includes free form of palmitoyl-Gly-His and is formulated with propylene glycol alginate

| | Formulation amount |
|---|---|
| Glycerin dispersion containing free form of palmitoyl-Gly-His at 5% | 1 g |
| 1% Aqueous propylene glycol alginate solution | 9 g |

Example 16

Feel in Use of Sprayable Gel-Form Cosmetic that Includes Free Form of Palmitoyl-Gly-His and is Formulated with Sodium Alginate 0.5 g of a glycerin dispersion containing a free form of palmitoyl-Gly-His at 5% was placed in a screw tube (manufactured by Maruemu Corporation, No. 5), and 4.5 g of 1% sodium alginate was added thereto. The resultant solution was heated in a dry bath incubator (manufactured by First Gene) (90° C., 20 minutes), and the resulting solution was transferred to a spray vial (manufactured by Maruemu Corporation, No. 3L), which was left to cool to reach room temperature.

A state in which, after cooling down, the solution lost fluidity and did not flow down when the spray vial was inverted was confirmed, and thus it was determined that the solution had been gelled. Evaluation of the feel in use is listed in Table 24.

TABLE 16

Sprayable gel-form cosmetic that includes free form of palmitoyl-Gly-His and is formulated with sodium alginate

| | Formulation amount |
|---|---|
| Glycerin dispersion containing free form of palmitoyl-Gly-His at 5% | 0.5 g |
| 1% Aqueous sodium alginate solution | 4.5 g |

Example 17

Feel in Use of Sprayable Gel-Form Cosmetic that Includes Free Form of Palmitoyl-Gly-His and is Formulated with Cellulose and Propylene Glycol Alginate 0.25 g of a glycerin dispersion containing a free form of palmitoyl-Gly-His at 5% was placed in a screw tube (manufactured by Maruemu Corporation, No. 5), and 5 g of a 2% aqueous cellulose solution and 4.75 g of 1% propylene glycol alginate were added thereto. The resultant solution was heated in a dry bath incubator (manufactured by First Gene) (80° C., 15 minutes), and the resulting solution was transferred to a spray vial (manufactured by Maruemu Corporation, No. 3L), which was left to cool to reach room temperature.

A state in which, after cooling down, the solution lost fluidity and did not flow down when the spray vial was inverted was confirmed, and thus it was determined that the solution had been gelled. Evaluation of the feel in use is listed in Table 24.

TABLE 17

Sprayable gel-form cosmetic that includes free form of palmitoyl-Gly-His and is formulated with cellulose and propylene glycol alginate

| | Formulation amount |
|---|---|
| Glycerin dispersion containing free form of palmitoyl-Gly-His at 5% | 0.25 g |
| 2% Aqueous cellulose solution | 5 g |
| 1% Aqueous propylene glycol alginate solution | 4.75 g |

Example 18

Feel in Use of Sprayable Gel-Form Cosmetic that Includes Free Form of Palmitoyl-Gly-His and is Formulated with Cellulose, Propylene Glycol Alginate, and Polyvinyl Alcohol 0.25 g of a glycerin dispersion containing a free form of palmitoyl-Gly-His at 5% and 0.25 g of a propylene glycol dispersion containing a free form of palmitoyl-Gly-His at 1% were placed in a screw tube (manufactured by Maruemu Corporation, No. 5), and 3 g of a 2% aqueous cellulose solution, 3 g of 1% propylene glycol alginate, 1 g of a 5% aqueous polyvinyl alcohol solution, and 2.5 g of deionized water were added thereto. The resultant solution was heated in a dry bath incubator (manufactured by First Gene) (80° C., 20 minutes), and the resulting solution was transferred to a spray vial (manufactured by Maruemu Corporation, No. 3L), which was left to cool to reach room temperature.

A state in which, after cooling down, the solution lost fluidity and did not flow down when the spray vial was inverted was confirmed, and thus it was determined that the solution had been gelled. Evaluation of the feel in use is listed in Table 24.

TABLE 18

Sprayable gel-form cosmetic that includes free form of palmitoyl-Gly-His and is formulated with cellulose, propylene glycol alginate, and polyvinyl alcohol

| | Formulation amount |
|---|---|
| Glycerin dispersion containing free form of palmitoyl-Gly-His at 5% | 0.25 g |
| Propylene glycol dispersion containing free form of palmitoyl-Gly-His at 1% | 0.25 g |
| 2% Aqueous cellulose solution | 3 g |
| 1% Aqueous propylene glycol alginate solution | 3 g |
| 5% Aqueous polyvinyl alcohol solution | 1 g |
| Deionized water | 2.5 g |

Example 19

Feel in Use of Gel-Form Cosmetic Obtained by Dispersing Free Form of Palmitoyl-Gly-His in Propylene Glycol Alginate at Room Temperature 0.3 g of the free form of palmitoyl-Gly-His synthesized in Synthesis Example 2 was placed in an agate mortar and was sufficiently pulverized. 15 g of 1% propylene glycol alginate was added thereto and the resultant solution was dispersed. The resultant solution was transferred to a screw tube (manufactured by Maruemu Corporation, No. 5).

A state in which, 16 hours later, the solution lost fluidity and did not flow down when the screw tube was inverted was confirmed, and thus it was determined that the solution had been gelled. Evaluation of the feel in use is listed in Table 24.

TABLE 19

Gel-form cosmetic obtained by dispersing free form of palmitoyl-Gly-His in propylene glycol alginate at room temperature

|  | Formulation amount |
|---|---|
| Dispersion containing free form of palmitoyl-Gly-His | 0.3 g |
| 1% Aqueous propylene glycol alginate solution | 15 g |

Example 20

Feel in Use of Meringue-Like, Gel-Form Cosmetic that Includes Free Form of Palmitoyl-Gly-His and is Formulated with Propylene Glycol Alginate 0.9 g of the free form of palmitoyl-Gly-His synthesized in Synthesis Example 2 was placed in a screw tube (manufactured by Maruemu Corporation, No. 7), and 29.1 g of 1% propylene glycol alginate was added thereto. The resultant solution was heated in a dry bath incubator (manufactured by First Gene) (80° C., 30 minutes), and the resulting dispersion was transferred to a glass petri dish (diameter: 6 cm, height: 4.5 cm), in which the dispersion was stirred with a magnetic stirrer (manufactured by Nissin) (500 rpm, 30 minutes) under an environment of 23° C.

A state in which, 24 hours later, the solution lost fluidity and did not flow down when the glass petri dish was inverted was confirmed, and thus it was determined that the solution had been gelled. Evaluation of the feel in use is listed in Table 24.

TABLE 20

Meringue-like, gel-form cosmetic that includes free form of palmitoyl-Gly-His and is formulated with propylene glycol alginate

|  | Formulation amount |
|---|---|
| Free form of palmitoyl-Gly-His | 0.9 g |
| 1% Aqueous propylene glycol alginate solution | 29.1 g |

Example 21

Feel in Use of Gel-Form Cosmetic that Includes Free Form of Palmitoyl-Gly-His and is Formulated with Collagen 4.5 g of the meringue-like gel-form cosmetic that includes a free form of palmitoyl-Gly-His and is formulated with propylene glycol alginate, obtained in Example 20, and 0.5 g of Seagem Collagen AS (manufactured by Katakura Chikkarin Co., Ltd.) were placed in a plastic jar (diameter: 3 cm, height: 2.5 cm), and the resultant solution was sufficiently mixed with a spatula under an environment of 23° C. to prepare a gel-form cosmetic that includes a free form of palmitoyl-Gly-His and is formulated with collagen. Evaluation of the feel in use is listed in Table 24.

TABLE 21

Gel-form cosmetic that includes free form of palmitoyl-Gly-His and is formulated with collagen

|  | Formulation amount |
|---|---|
| Meringue-like gel-form cosmetic that includes free form of palmitoyl-Gly-His and is formulated with propylene glycol alginate | 4.5 g |
| Collagen | 0.5 g |

Example 22

Feel in Use of Gel-Form Cosmetic that Includes Free Form of Palmitoyl-Gly-His and is Formulated with Sodium Hyaluronate 4 g of the meringue-like gel-form cosmetic that includes a free form of palmitoyl-Gly-His and is formulated with propylene glycol alginate, obtained in Example 20, and 1 g of a 1% aqueous Hyaluronic Acid FCH solution (sodium hyaluronate manufactured by Kibun Food Chemifa Co., Ltd.) were placed in a plastic jar (diameter: 3 cm, height: 2.5 cm), and the resultant solution was sufficiently mixed with a spatula under an environment of 23° C. to prepare a gel-form cosmetic that includes a free form of palmitoyl-Gly-His and is formulated with hyaluronic acid. Evaluation of the feel in use is listed in Table 24.

TABLE 22

Gel-form cosmetic that includes free form of palmitoyl-Gly-His and is formulated with sodium hyaluronate

|  | Formulation amount |
|---|---|
| Meringue-like gel-form cosmetic that includes free form of palmitoyl-Gly-His and is formulated with propylene glycol alginate | 4 g |
| 1% Sodium hyaluronate | 1 g |

Example 23

Feel in Use of Gel-Form Cosmetic that Includes Free Form of Palmitoyl-Gly-His and is Formulated with Methylcellulose 4 g of the meringue-like gel-form cosmetic that includes a free form of palmitoyl-Gly-His and is formulated with propylene glycol alginate, obtained in Example 20, and 1 g of a 0.5% methylcellulose solution were placed in a plastic jar (diameter: 3 cm, height: 2.5 cm), and the resultant solution was sufficiently mixed with a spatula under an environment of 23° C. to prepare a gel-form cosmetic that includes a free faint of palmitoyl-Gly-His and is formulated with methylcellulose. Evaluation of the feel in use is listed in Table 24.

TABLE 23

Gel-form cosmetic that includes free form of palmitoyl-Gly-His and is formulated with methylcellulose

| | Formulation amount |
|---|---|
| Meringue-like gel-form cosmetic that includes free form of palmitoyl-Gly-His and is formulated with propylene glycol alginate | 4 g |
| 0.5% Aqueous methylcellulose solution | 1 g |

TABLE 24

Evaluation results of feel in use in Examples 14 to 23

| | Example | | | | | | | | | |
|---|---|---|---|---|---|---|---|---|---|---|
| | 14 | 15 | 16 | 17 | 18 | 19 | 20 | 21 | 22 | 23 |
| Stretching on skin surface | ○ | ○ | ○ | ○ | ○ | ○ | ○ | ○ | ○ | ○ |
| Permeation into skin | ○ | ○ | ○ | ○ | ○ | ○ | ○ | ○ | ○ | ○ |
| Stickiness | ○ | ○ | ○ | ○ | ○ | ○ | ○ | ○ | ○ | ○ |
| Crinkles | Δ | Δ | Δ | Δ to ○ | Δ to ○ | Δ | Δ | Δ | Δ | Δ |

According to the results of Examples 14 to 23 in Table 24, gels that include the lipid peptide-based gelator of the present invention and water or a functional material such as polymers had a feel in use, e.g., excellent stretching on the skin surface, excellent permeation into the skin, and no lingering stickiness.

Example 24

Feel in Use of Sprayable Gel-Form Cosmetic that Includes Free Form of Palmitoyl-Gly-His and is Formulated with Cellulose and Propylene Glycol Alginate 0.5 g of a glycerin dispersion containing a free form of palmitoyl-Gly-His at 5% was placed in a screw tube (manufactured by Maruemu Corporation, No. 5), and 4.5 g of a 2% aqueous cellulose solution was added thereto. The resultant solution was heated in a dry bath incubator (manufactured by First Gene) (90° C., 20 minutes), and the resulting solution was transferred to a spray vial (manufactured by Maruemu Corporation, No. 3L) and was left to cool to reach room temperature.

A state in which, after cooling down, the solution lost fluidity and did not flow down when the spray vial was inverted was confirmed, and thus it was determined that the solution had been gelled. Evaluation of the feel in use is listed in Table 27.

TABLE 25

Sprayable gel-form cosmetic that includes free form of palmitoyl-Gly-His and is formulated with cellulose and propylene glycol alginate

| | Formulation amount |
|---|---|
| Glycerin dispersion containing a free form of palmitoyl-Gly-His at 5% | 0.5 g |
| 2% Aqueous cellulose solution | 4.5 g |

Example 25

Feel in Use of Whipped Cream-Like Gel-Form Cosmetic that Includes Free Form of Palmitoyl-Gly-His and is Formulated with Propylene Glycol Alginate 0.9 g of the free form of palmitoyl-Gly-His synthesized in Synthesis Example 2 was placed in a screw tube (manufactured by Maruemu Corporation, No. 7), and 29.1 g of 1% propylene glycol alginate was added thereto. The resultant solution was heated in a dry bath incubator (manufactured by First Gene) (80° C., 30 minutes), and the resulting dispersion was transferred to a glass petri dish (manufactured by Maruemu Corporation, No. 3L), in which the dispersion was stirred (200 rpm, 10 minutes) at room temperature.

A state in which, 24 hours later, the solution lost fluidity and did not flow down when the glass petri dish was inverted was confirmed, and thus it was determined that the solution had been gelled. Evaluation of the feel in use is listed in Table 27.

TABLE 26

Whipped cream-like gel-form cosmetic that includes free form of palmitoyl-Gly-His and is formulated with propylene glycol alginate

| | Formulation amount |
|---|---|
| Free form of palmitoyl-Gly-His | 0.9 g |
| 1% Aqueous propylene glycol alginate solution | 2.91 g |
| Deionized water | 26.19 g |

TABLE 27

Evaluation results of feel in use in Examples 24 and 25

| | Example | |
|---|---|---|
| | 24 | 25 |
| Stretching on skin surface | ○ | ○ |
| Permeation into skin | ○ | ○ |
| Stickiness | ○ | ○ |
| Crinkles | Δ | Δ to ○ |

According to the results of Examples 24 and 25 in Table 27, gels that include the lipid peptide-based gelator of the present invention and water or a functional material such as polymers had a feel in use, e.g., excellent stretching on the skin surface, excellent permeation into the skin, and no lingering stickiness.

[Evaluation of Hemostatic Effect]

A medical instrument that is formulated with a macromolecular compound having blood coagulating activity was prepared according to Examples 26 to 29, and the hemostatic effect of the medical instrument was evaluated. Evaluation results are listed in Table 29.

[Reference Example 1 and Examples 26 to 29: Evaluation of Free Form of Palmitoyl-Gly-His as Medical Instrument]

To a 50 mM phosphate buffer solution (pH 7.5) that was used as a solvent, the free form of palmitoyl-Gly-His synthesized in Synthesis Example 2 was added to achieve a final concentration thereof in 1 mL of the solvent of 0.3% (w/v), and the blood coagulating substances listed in Table 24 was added to achieve a final concentration thereof in 1 mL of the solvent of 1% (w/v). The resultant solution was mixed and was then heated so as to dissolve the resultant. The mixture was then transferred to a petri dish and gelation was confirmed, followed by making a hole with a diameter of 7 mm and a depth of 5 mm at the center of the gel. 150 μL of guinea pig blood stored was dropped into the hole, and the resultant blood was left still standing overnight at room temperature, followed by evaluating blood coagulation (hemostatic effect) by visual observation.

The stored guinea pig blood used was prepared as a sample immediately after blood was drawn in a sterile manner, to have a proportion of a storage solution for inhibiting coagulation to the blood of 1:1. The composition of the storage solution was 5.5 g of citric acid, 80.0 g of sodium citrate, 42.0 g of sodium chloride, and 205.0 g of dextrose that were dissolved in 10 L of purified water.

Evaluation of blood coagulation (hemostatic effect) is listed in Table 29 and FIGS. 3 to 6.

TABLE 28

Blood coagulating substances used in evaluation of medical instrument that includes free form of palmitoyl-Gly-His

| | Blood coagulating substance |
|---|---|
| Reference Example 1 | None |
| Example 26 | Gelatin |
| Example 27 | Sodium alginate |
| Example 28 | Propylene glycol alginate |
| Example 29 | Gum arabic |

[Reference Example 2 and Comparative Examples 6 to 9: Evaluation of Carboxymethylcellulose (Hereinafter, also Called "CMC") as Medical Instrument]

Blood coagulation (hemostatic effect) was evaluated in the same conditions as in Reference Example 1 and Examples 26 to 29 except that carboxymethylcellulose was used instead of the gelator. Evaluation of blood coagulation (hemostatic effect) is listed in Table 29 and shown in FIGS. 3 to 6.

TABLE 29

Evaluation results of blood coagulation (hemostatic effect)

| Blood coagulating substance (1%) | | 1% Pal-GH | | 10% CMC |
|---|---|---|---|---|
| None | Reference Example 1 | Blood leached out into gel | Reference Example 2 | Entire blood gelled by CMC |
| Gelatin | Example 26 | Blood coagulation was observed starting at contacting area | Comparative Example 6 | Entire blood gelled by CMC |
| Sodium alginate | Example 27 | Blood coagulation was observed starting at contacting area | Comparative Example 7 | Entire blood gelled by CMC |
| Propylene glycol alginate | Example 28 | Blood coagulation was observed starting at contacting area | Comparative Example 8 | Entire blood gelled by CMC |
| Gum arabic | Example 29 | Blood coagulated | Comparative Example 9 | Entire blood gelled by CMC |

According to the results of Reference Example 1 in Table 29, in the case of a gelator alone, no blood coagulation was observed and blood leached out into the gel, whereby the gel included the blood. In contrast, according to the results of Examples 26 to 29, the medical instrument of the present invention exhibited an excellent hemostatic effect. In Comparative Examples 6 to 9 which used, as a gelator, carboxymethylcellulose that is a food thickener and is widely applied in the industrial field, the entire blood gelled by carboxymethylcellulose, and therefore an hemostatic effect was not obtained.

INDUSTRIAL APPLICABILITY

The cosmetic or the external skin preparation of the present invention that is formulated with a lipid peptide-based gelator, in which the lipid peptide has a low molecular weight, achieves an improved feel in use, e.g., excellent stretching on the skin surface and the hair surface and excellent permeation into the skin and the hair when applied on the skin and the hair, and no stickiness or crinkles, and when the cosmetic or the external skin preparation is in a liquid form or other dosage form, causes no dripping. Therefore, the cosmetic or the external skin preparation of the present invention is expected to be widely used as a cosmetic or an external skin preparation.

The cosmetic or the external skin preparation of the present invention that is formulated with a lipid peptide-based gelator, in which the lipid peptide has a low molecular weight, and a macromolecular compound achieves an improved feel in use, e.g., excellent stretching on the skin surface and the hair surface, excellent permeation into the skin and the hair, and no lingering stickiness, and therefore is expected to be widely used as a cosmetic or an external skin preparation.

Furthermore, the cosmetic, the external skin preparation, and the medical instrument of the present invention that are formulated with a lipid peptide-based gelator, in which the lipid peptide has a low molecular weight, and a macromolecular compound achieve a synergistic effect of the lipid peptide-based gelator and the macromolecular compound. For example, using a macromolecular compound having blood coagulating activity as the macromolecular compound, the effect of the lipid peptide-based gelator to form a fiber which causes physical hemostasis of blood cells and the effect of the macromolecular compound to form a blood clot are obtained. Therefore, the medical instrument of the present invention has an excellent hemostatic effect and is expected to be utilized as a wound dressing base material or a hemostatic agent base material.

The invention claimed is:

1. A method for coagulating blood with a medical instrument, the medical instrument comprising:
at least one lipid peptide-based gelator that contains a lipid peptide or a pharmaceutically usable salt thereof; and
at least one macromolecular compound having blood coagulating activity, wherein:
the lipid peptide is represented by Formula (1):

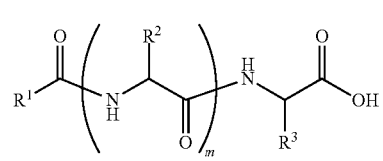

where:
- $R^1$ is a $C_{9-23}$ aliphatic group;
- $R^2$ and $R^3$ are independently a hydrogen atom, a methyl group, an ethyl group, a $C_{3-7}$ alkyl group that optionally contains a $C_{1-3}$ branched chain, a phenylmethyl group, a phenylethyl group, or a —$(CH_2)_n$—X group;
- at least one of $R^2$ and $R^3$ is a —$(CH_2)_n$—X group;
- n is a number of 1 to 4;
- X is an amino group, a guanidino group, a carbamoyl group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms; and
- m is 1, wherein the macromolecular compound having blood coagulating activity is gum arabic, and wherein a concentration of the gum arabic is 0.1 to 3% (w/v) relative to the total volume of the medical instrument, the method comprising:
  contacting the medical instrument with blood, and coagulating the blood.

* * * * *